(12) United States Patent
Trull et al.

(10) Patent No.: US 8,032,996 B2
(45) Date of Patent: Oct. 11, 2011

(54) APPARATUS FOR FORMING BARBS ON A SUTURE

(75) Inventors: Michael Trull, Apex, NC (US); Perry A. Genova, Chapel Hill, NC (US); Robert C. Williams, III, Raleigh, NC (US); Jeffrey C. Leung, Raleigh, NC (US); Matthew A. Megaro, Chapel Hill, NC (US); Stanton Batchelor, Holly Springs, NC (US); Andrew Corson, Apex, NC (US)

(73) Assignee: Quill Medical, Inc.

( * ) Notice: Subject to any disclaimer, the term of this patent is extended or adjusted under 35 U.S.C. 154(b) by 1371 days.

(21) Appl. No.: 10/556,419

(22) PCT Filed: May 13, 2004

(86) PCT No.: PCT/US2004/014962
§ 371 (c)(1),
(2), (4) Date: Aug. 9, 2006

(87) PCT Pub. No.: WO2004/100801
PCT Pub. Date: Nov. 25, 2004

(65) Prior Publication Data
US 2007/0065663 A1    Mar. 22, 2007

(51) Int. Cl.
*B21F 25/00* (2006.01)
(52) U.S. Cl. .......................................... 29/7.1
(58) Field of Classification Search ............. 29/7.1, 29/7, 2, 7.3; 83/651; 606/228, 215, 226, 606/216; 428/357
See application file for complete search history.

(56) References Cited

U.S. PATENT DOCUMENTS

| | | | |
|---|---|---|---|
| 709,392 A | 9/1902 | Brown |
| 733,723 A | 7/1903 | Lukens |
| 789,401 A | 5/1905 | Acheson |
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Wachenfeldt |
| 1,886,721 A | 11/1932 | O'Brien |

(Continued)

FOREIGN PATENT DOCUMENTS

BE    1014364    9/2003

(Continued)

OTHER PUBLICATIONS

International Search Report for PCT/US2007/074658 dated Jun. 12, 2007, 3 pages.

(Continued)

*Primary Examiner* — John C Hong
(74) *Attorney, Agent, or Firm* — Angiotech

(57) ABSTRACT

An apparatus for cutting barbs into a suture having a filament supply. The apparatus also has an in-feed collet for holding one end of a filament threaded therethrough. Further the apparatus has an out-feed collet for holding a second end of a filament threaded therethrough. Additionally, the apparatus has a holder positioned between said in-feed and out-feed collets for holding a filament suspended between the in-feed and out-feed collets. The apparatus also has a cutting assembly for cutting barbs in the filament tensioned between the in-feed and out-feed collets.

16 Claims, 22 Drawing Sheets

U.S. PATENT DOCUMENTS

| | | |
|---|---|---|
| 2,094,578 A | 10/1937 | Blumenthal |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,472,009 A | 5/1949 | Gardner |
| 2,480,271 A * | 8/1949 | Sumner .......................... 83/147 |
| 2,572,936 A | 10/1951 | Kulp |
| 2,684,070 A | 7/1954 | Kelsey |
| 2,779,083 A | 1/1957 | Eaton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,988,028 A | 6/1961 | Alcamo |
| 3,003,155 A | 10/1961 | Mielzynski |
| 3,068,869 A | 12/1962 | Shelden |
| 3,068,870 A | 12/1962 | Levin |
| 3,123,077 A | 3/1964 | Alcamo |
| 3,166,072 A | 1/1965 | Sullivan |
| 3,187,752 A | 6/1965 | Glick |
| 3,206,018 A | 9/1965 | Lewis |
| 3,209,652 A | 10/1965 | Burgsmueller |
| 3,209,754 A | 10/1965 | Brown |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | Le Roy |
| 3,494,006 A | 2/1970 | Brumlik |
| 3,525,340 A | 8/1970 | Gilbert |
| 3,527,223 A | 9/1970 | Shein |
| 3,545,608 A | 12/1970 | Berger |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | deMestral |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,918,455 A | 11/1975 | Coplan |
| 3,951,261 A | 4/1976 | Mandel |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen |
| 4,006,747 A | 2/1977 | Kronenthal |
| 4,008,303 A | 2/1977 | Glick |
| 4,027,608 A | 6/1977 | Arbuckle |
| 4,043,344 A | 8/1977 | Landi |
| D246,911 S | 1/1978 | Bess, Jr. |
| 4,069,825 A | 1/1978 | Akiyama |
| 4,073,298 A | 2/1978 | Le Roy |
| 4,137,921 A | 2/1979 | Okuzumi |
| 4,198,734 A | 4/1980 | Brumlik |
| 4,204,541 A | 5/1980 | Kapitanov |
| 4,204,542 A | 5/1980 | Bokros |
| 4,259,959 A | 4/1981 | Walker |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin |
| 4,428,376 A | 1/1984 | Mericle |
| 4,430,998 A | 2/1984 | Harvey |
| 4,434,796 A | 3/1984 | Karapetian |
| 4,454,875 A | 6/1984 | Pratt |
| 4,467,805 A | 8/1984 | Fukuda |
| 4,492,075 A | 1/1985 | Faure |
| 4,493,323 A | 1/1985 | Albright |
| 4,505,274 A | 3/1985 | Speelman |
| 4,510,934 A | 4/1985 | Batra |
| 4,531,522 A | 7/1985 | Bedi |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards |
| 4,676,245 A | 6/1987 | Fukuda |
| 4,719,917 A | 1/1988 | Barrows |
| 4,741,330 A | 5/1988 | Hayhurst |
| 4,750,910 A | 6/1988 | Takayanagi |
| 4,751,621 A | 6/1988 | Jenkins |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays |
| 4,898,156 A | 2/1990 | Gatturna |
| 4,899,743 A | 2/1990 | Nicholson |
| 4,900,605 A | 2/1990 | Thorgersen |
| 4,905,367 A | 3/1990 | Pinchuk et al. |
| 4,930,945 A | 6/1990 | Arai |
| 4,932,962 A | 6/1990 | Yoon |
| 4,946,468 A | 8/1990 | Li |
| 4,948,444 A | 8/1990 | Schutz et al. |
| 4,950,258 A | 8/1990 | Kawai |
| 4,950,285 A | 8/1990 | Wilk |
| 4,968,315 A | 11/1990 | Gatturna |
| 4,976,715 A | 12/1990 | Bays |
| 4,981,149 A | 1/1991 | Yoon |
| 4,994,073 A | 2/1991 | Green |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen |
| 5,026,390 A | 6/1991 | Brown |
| 5,037,422 A | 8/1991 | Hayhurst |
| 5,041,129 A | 8/1991 | Hayhurst |
| 5,046,513 A | 9/1991 | Gatturna |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson |
| 5,102,418 A | 4/1992 | Granger |
| 5,102,421 A | 4/1992 | Anspach, Jr. |
| 5,103,073 A | 4/1992 | Danilov |
| 5,112,344 A | 5/1992 | Petros |
| 5,123,911 A | 6/1992 | Granger |
| 5,123,913 A | 6/1992 | Wilk |
| 5,123,919 A | 6/1992 | Sauter |
| 5,127,413 A | 7/1992 | Ebert |
| 5,133,738 A | 7/1992 | Korthoff |
| 5,141,520 A | 8/1992 | Goble |
| 5,147,382 A | 9/1992 | Gertzman |
| 5,156,788 A | 10/1992 | Chesterfield |
| 5,176,692 A | 1/1993 | Wilk |
| 5,179,964 A | 1/1993 | Cook |
| 5,192,274 A | 3/1993 | Bierman |
| 5,192,302 A | 3/1993 | Kensey |
| 5,192,303 A | 3/1993 | Gatturna |
| 5,197,597 A | 3/1993 | Leary |
| 5,207,679 A | 5/1993 | Li |
| 5,207,694 A | 5/1993 | Broome |
| 5,217,486 A | 6/1993 | Rice |
| 5,217,494 A | 6/1993 | Coggins |
| 5,222,508 A | 6/1993 | Contarini |
| 5,222,976 A | 6/1993 | Yoon |

| | | | | | |
|---|---|---|---|---|---|
| 5,224,946 A | 7/1993 | Hayhurst | D387,161 S | 12/1997 | Ferragamo |
| 5,242,457 A | 9/1993 | Akopov | 5,697,976 A | 12/1997 | Chesterfield |
| 5,246,441 A | 9/1993 | Ross | 5,702,462 A | 12/1997 | Oberlander |
| 5,249,673 A | 10/1993 | Sinn | 5,709,692 A | 1/1998 | Mollenauer |
| 5,258,013 A | 11/1993 | Granger | 5,716,358 A | 2/1998 | Ochoa |
| 5,263,973 A | 11/1993 | Cook | 5,716,376 A | 2/1998 | Roby |
| 5,269,783 A | 12/1993 | Sander | 5,722,991 A | 3/1998 | Colligan |
| 5,282,832 A | 2/1994 | Toso | 5,723,008 A | 3/1998 | Gordon |
| 5,292,326 A | 3/1994 | Green | 5,725,557 A | 3/1998 | Gatturna |
| 5,306,288 A | 4/1994 | Granger | 5,728,114 A | 3/1998 | Evans |
| 5,306,290 A | 4/1994 | Martins | 5,741,277 A | 4/1998 | Gordon |
| 5,320,629 A | 6/1994 | Noda | 5,763,411 A | 6/1998 | Edwardson |
| 5,330,488 A | 7/1994 | Goldrath | 5,765,560 A | 6/1998 | Verkerke |
| 5,330,503 A | 7/1994 | Yoon | 5,779,719 A | 7/1998 | Klein |
| 5,336,239 A | 8/1994 | Gimpelson | 5,782,864 A | 7/1998 | Lizardi |
| 5,341,922 A | 8/1994 | Cerwin | 5,807,403 A | 9/1998 | Beyar |
| 5,342,376 A | 8/1994 | Ruff | 5,807,406 A | 9/1998 | Brauker |
| 5,342,395 A | 8/1994 | Jarrett | 5,810,853 A | 9/1998 | Yoon |
| 5,352,515 A | 10/1994 | Jarrett | 5,814,051 A | 9/1998 | Wenstrom, Jr. |
| 5,354,271 A | 10/1994 | Voda | 5,843,087 A | 12/1998 | Jensen |
| 5,354,298 A | 10/1994 | Lee | 5,843,178 A | 12/1998 | Vanney |
| 5,358,511 A | 10/1994 | Gatturna | 5,863,360 A | 1/1999 | Wood |
| 5,363,556 A * | 11/1994 | Banholzer et al. ....... 29/890.142 | 5,884,859 A | 3/1999 | Ma |
| 5,372,146 A | 12/1994 | Branch | 5,887,594 A | 3/1999 | LoCicero, III |
| 5,374,268 A | 12/1994 | Sander | 5,891,166 A | 4/1999 | Schervinsky |
| 5,374,278 A | 12/1994 | Chesterfield | 5,893,856 A | 4/1999 | Jacob |
| 5,380,334 A | 1/1995 | Torrie | 5,895,395 A | 4/1999 | Yeung |
| 5,391,173 A | 2/1995 | Wilk | 5,895,413 A | 4/1999 | Nordstrom |
| 5,395,126 A | 3/1995 | Tresslar | 5,897,572 A | 4/1999 | Schulsinger |
| 5,403,346 A | 4/1995 | Loeser | 5,899,911 A | 5/1999 | Carter |
| 5,411,523 A | 5/1995 | Goble | 5,916,224 A | 6/1999 | Esplin |
| 5,414,988 A | 5/1995 | Di Palma | 5,919,234 A | 7/1999 | Lemperle |
| 5,417,691 A | 5/1995 | Hayhurst | 5,921,982 A | 7/1999 | Lesh |
| 5,425,746 A | 6/1995 | Proto | 5,925,078 A | 7/1999 | Anderson |
| 5,425,747 A | 6/1995 | Brotz | 5,931,855 A * | 8/1999 | Buncke ................. 606/228 |
| 5,437,680 A | 8/1995 | Yoon | 5,935,138 A | 8/1999 | McJames, II |
| 5,450,860 A | 9/1995 | O'Connor | 5,938,668 A | 8/1999 | Scirica |
| 5,451,461 A | 9/1995 | Broyer | 5,950,633 A | 9/1999 | Lynch |
| 5,462,561 A | 10/1995 | Voda | 5,954,747 A | 9/1999 | Clark |
| 5,464,427 A | 11/1995 | Curtis | 5,968,097 A | 10/1999 | Frechet |
| 5,472,452 A | 12/1995 | Trott | 5,972,024 A | 10/1999 | Northrup, III |
| 5,478,353 A | 12/1995 | Yoon | 5,984,933 A | 11/1999 | Yoon |
| 5,480,403 A | 1/1996 | Lee | 5,993,459 A | 11/1999 | Larsen |
| 5,480,411 A | 1/1996 | Liu | 6,001,111 A | 12/1999 | Sepetka |
| 5,484,451 A | 1/1996 | Akopov | 6,012,216 A | 1/2000 | Esteves |
| 5,486,197 A | 1/1996 | Le | 6,015,410 A | 1/2000 | Tormala |
| 5,494,154 A | 2/1996 | Ainsworth | 6,024,757 A | 2/2000 | Haase |
| 5,500,000 A | 3/1996 | Feagin | 6,027,523 A | 2/2000 | Schmieding |
| 5,500,991 A | 3/1996 | Demarest | 6,039,741 A | 3/2000 | Meislin |
| 5,520,084 A | 5/1996 | Chesterfield | 6,056,778 A | 5/2000 | Grafton |
| 5,520,691 A | 5/1996 | Branch | 6,063,105 A | 5/2000 | Totakura |
| 5,522,845 A | 6/1996 | Wenstrom, Jr. | 6,074,419 A | 6/2000 | Healy |
| 5,531,760 A | 7/1996 | Alwafaie | 6,076,255 A | 6/2000 | Shikakubo |
| 5,531,761 A | 7/1996 | Yoon | 6,083,244 A | 7/2000 | Lubbers |
| 5,531,790 A | 7/1996 | Frechet | 6,102,947 A | 8/2000 | Gordon |
| 5,533,982 A | 7/1996 | Rizk | 6,106,544 A | 8/2000 | Brazeau |
| 5,536,582 A | 7/1996 | Prasad | D433,753 S | 11/2000 | Weiss |
| 5,540,705 A | 7/1996 | Meade | 6,146,406 A | 11/2000 | Shluzas |
| 5,540,718 A | 7/1996 | Bartlett | 6,146,407 A | 11/2000 | Krebs |
| 5,546,957 A | 8/1996 | Heske | 6,149,660 A | 11/2000 | Laufer |
| 5,554,171 A | 9/1996 | Gatturna | 6,163,948 A | 12/2000 | Esteves |
| 5,566,822 A | 10/1996 | Scanlon | 6,165,203 A | 12/2000 | Krebs |
| 5,571,175 A | 11/1996 | Vanney | 6,168,633 B1 | 1/2001 | Shoher |
| 5,571,216 A | 11/1996 | Anderson | 6,174,324 B1 | 1/2001 | Egan |
| 5,573,543 A | 11/1996 | Akopov | 6,183,499 B1 | 2/2001 | Fischer |
| 5,584,859 A | 12/1996 | Brotz | 6,187,095 B1 | 2/2001 | Labrecque |
| 5,601,557 A | 2/1997 | Hayhurst | 6,206,908 B1 | 3/2001 | Roby |
| 5,626,590 A | 5/1997 | Wilk | 6,235,869 B1 | 5/2001 | Roby |
| 5,632,753 A | 5/1997 | Loeser | 6,241,747 B1 | 6/2001 | Ruff |
| 5,643,288 A | 7/1997 | Thompson | 6,251,143 B1 | 6/2001 | Schwartz |
| 5,643,295 A | 7/1997 | Yoon | 6,264,675 B1 | 7/2001 | Brotz |
| 5,643,319 A | 7/1997 | Green | 6,267,772 B1 | 7/2001 | Mulhauser |
| 5,647,874 A | 7/1997 | Hayhurst | 6,270,517 B1 | 8/2001 | Brotz |
| 5,649,939 A | 7/1997 | Reddick | 6,315,788 B1 | 11/2001 | Roby |
| 5,653,716 A | 8/1997 | Malo | 6,319,231 B1 | 11/2001 | Andrulitis |
| 5,662,714 A | 9/1997 | Charvin | 6,334,865 B1 | 1/2002 | Redmond |
| 5,669,935 A | 9/1997 | Rosenman | 6,387,363 B1 | 5/2002 | Gruskin |
| D386,583 S | 11/1997 | Ferragamo | 6,388,043 B1 | 5/2002 | Langer |
| 5,683,417 A | 11/1997 | Cooper | 6,395,029 B1 | 5/2002 | Levy |

| Patent No. | Date | Name |
|---|---|---|
| D462,766 S | 9/2002 | Jacobs |
| 6,443,962 B1 | 9/2002 | Gaber |
| 6,463,719 B2 | 10/2002 | Dey |
| 6,471,715 B1 | 10/2002 | Weiss |
| 6,478,809 B1 | 11/2002 | Brotz |
| 6,485,503 B2 | 11/2002 | Jacobs |
| 6,491,701 B2 | 12/2002 | Tierney |
| 6,494,898 B1 | 12/2002 | Roby |
| 6,495,127 B1 | 12/2002 | Wallace |
| RE37,963 E | 1/2003 | Thal |
| 6,506,190 B1 | 1/2003 | Walshe |
| 6,511,488 B1 | 1/2003 | Marshall |
| 6,514,265 B2 | 2/2003 | Ho |
| 6,527,795 B1 | 3/2003 | Lizardi |
| 6,551,343 B1 | 4/2003 | Tormala |
| 6,554,802 B1 | 4/2003 | Pearson |
| 6,565,597 B1 | 5/2003 | Fearnot |
| 6,592,609 B1 | 7/2003 | Bonutti |
| 6,596,296 B1 | 7/2003 | Nelson |
| 6,599,310 B2 | 7/2003 | Leung |
| 6,607,541 B1 | 8/2003 | Gardiner |
| 6,610,078 B1 | 8/2003 | Bru-Magniez |
| 6,613,059 B2 | 9/2003 | Schaller |
| 6,613,254 B1 | 9/2003 | Shiffer |
| 6,616,982 B2 | 9/2003 | Merrill |
| 6,623,492 B1 | 9/2003 | Berube |
| 6,626,930 B1 | 9/2003 | Allen |
| 6,641,592 B1 | 11/2003 | Sauer |
| 6,641,593 B1 | 11/2003 | Schaller |
| 6,645,226 B1 | 11/2003 | Jacobs |
| 6,645,227 B2 | 11/2003 | Fallin |
| 6,648,921 B2 | 11/2003 | Anderson |
| 6,656,182 B1 | 12/2003 | Hayhurst |
| 6,689,153 B1 | 2/2004 | Skiba |
| 6,702,844 B1 | 3/2004 | Lazarus |
| 6,712,830 B2 | 3/2004 | Esplin |
| 6,716,234 B2 | 4/2004 | Grafton |
| 6,720,402 B2 | 4/2004 | Langer |
| 6,726,705 B2 | 4/2004 | Peterson |
| 6,746,443 B1 | 6/2004 | Morley |
| 6,746,458 B1 | 6/2004 | Cloud |
| 6,749,616 B1 | 6/2004 | Nath |
| 6,773,450 B2 | 8/2004 | Leung |
| 6,783,554 B2 | 8/2004 | Amara |
| 6,814,748 B1 | 11/2004 | Baker |
| 6,818,010 B2 | 11/2004 | Eichhorn |
| 6,838,493 B2 | 1/2005 | Williams |
| 6,848,152 B2 | 2/2005 | Genova |
| 6,852,825 B2 | 2/2005 | Lendlein |
| 6,858,222 B2 | 2/2005 | Nelson |
| 6,860,891 B2 | 3/2005 | Schulze |
| 6,860,901 B1 | 3/2005 | Baker |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman |
| 6,911,035 B1 | 6/2005 | Blomme |
| 6,911,037 B2 | 6/2005 | Gainor |
| 6,913,607 B2 | 7/2005 | Ainsworth |
| 6,921,811 B2 | 7/2005 | Zamora |
| 6,923,819 B2 | 8/2005 | Meade |
| 6,945,021 B2 * | 9/2005 | Michel ............................ 56/249 |
| 6,945,980 B2 | 9/2005 | Nguyen |
| 6,960,221 B2 | 11/2005 | Ho |
| 6,960,233 B1 | 11/2005 | Berg |
| 6,974,450 B2 | 12/2005 | Weber |
| 6,981,983 B1 | 1/2006 | Rosenblatt |
| 6,984,241 B2 | 1/2006 | Lubbers |
| 6,986,780 B2 | 1/2006 | Rudnick |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson |
| 7,037,984 B2 | 5/2006 | Lendlein |
| 7,048,748 B1 | 5/2006 | Ustuner |
| 7,056,331 B2 | 6/2006 | Kaplan |
| 7,056,333 B2 | 6/2006 | Walshe |
| 7,057,135 B2 | 6/2006 | Li |
| 7,070,610 B2 | 7/2006 | Im |
| 7,081,135 B2 | 7/2006 | Smith |
| 7,083,637 B1 | 8/2006 | Tannhauser |
| 7,083,648 B2 | 8/2006 | Yu |
| 7,107,090 B2 | 9/2006 | Salisbury, Jr. |
| 7,112,214 B2 | 9/2006 | Peterson |
| 7,125,403 B2 | 10/2006 | Julian |
| 7,125,413 B2 | 10/2006 | Grigoryants |
| D532,107 S | 11/2006 | Peterson |
| 7,138,441 B1 | 11/2006 | Zhang |
| 7,141,302 B2 | 11/2006 | Mueller |
| 7,144,401 B2 | 12/2006 | Yamamoto |
| 7,144,412 B2 | 12/2006 | Wolf et al. |
| 7,144,415 B2 | 12/2006 | Del Rio |
| 7,150,757 B2 | 12/2006 | Fallin |
| 7,156,858 B2 | 1/2007 | Schuldt-Hempe |
| 7,156,862 B2 | 1/2007 | Jacobs |
| 7,160,312 B2 | 1/2007 | Saadat |
| 7,166,570 B2 | 1/2007 | Hunter |
| 7,172,595 B1 | 2/2007 | Goble |
| 7,172,615 B2 | 2/2007 | Morriss |
| 7,186,262 B2 | 3/2007 | Saadat |
| 7,195,634 B2 | 3/2007 | Schmieding |
| 7,211,088 B2 | 5/2007 | Grafton |
| 7,214,230 B2 | 5/2007 | Brock |
| 7,217,744 B2 | 5/2007 | Lendlein |
| 7,225,512 B2 | 6/2007 | Genova |
| 7,226,468 B2 | 6/2007 | Ruff |
| 7,232,447 B2 | 6/2007 | Gellman |
| 7,244,270 B2 | 7/2007 | Lesh |
| 7,279,612 B1 | 10/2007 | Heaton |
| 7,297,142 B2 | 11/2007 | Brock |
| 7,322,105 B2 | 1/2008 | Lewis |
| 7,371,253 B2 | 5/2008 | Leung |
| 7,513,904 B2 | 4/2009 | Sulamanidze |
| 7,514,095 B2 | 4/2009 | Nelson |
| 7,582,105 B2 | 9/2009 | Kolster |
| 7,601,164 B2 | 10/2009 | Wu |
| 7,624,487 B2 | 12/2009 | Trull |
| 2001/0011187 A1 | 8/2001 | Pavcnik |
| 2001/0018599 A1 | 8/2001 | D'Aversa |
| 2001/0039450 A1 | 11/2001 | Pavcnik |
| 2001/0044637 A1 | 11/2001 | Jacobs |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs |
| 2002/0029066 A1 | 3/2002 | Foerster |
| 2002/0069617 A1 | 6/2002 | Dey |
| 2002/0077448 A1 | 6/2002 | Antal |
| 2002/0077631 A1 | 6/2002 | Lubbers |
| 2002/0095164 A1 | 7/2002 | Andreas |
| 2002/0099394 A1 | 7/2002 | Houser |
| 2002/0111641 A1 | 8/2002 | Peterson |
| 2002/0111688 A1 | 8/2002 | Cauthen |
| 2002/0138009 A1 | 9/2002 | Brockway |
| 2002/0151980 A1 | 10/2002 | Cauthen |
| 2002/0173807 A1 | 11/2002 | Jacobs |
| 2002/0173822 A1 | 11/2002 | Justin |
| 2002/0179718 A1 | 12/2002 | Murokh |
| 2003/0014077 A1 | 1/2003 | Leung |
| 2003/0040795 A1 | 2/2003 | Elson |
| 2003/0041426 A1 | 3/2003 | Genova |
| 2003/0065360 A1 | 4/2003 | Jacobs |
| 2003/0065402 A1 | 4/2003 | Anderson |
| 2003/0069602 A1 | 4/2003 | Jacobs |
| 2003/0074021 A1 | 4/2003 | Morriss |
| 2003/0074023 A1 | 4/2003 | Kaplan |
| 2003/0078604 A1 | 4/2003 | Walshe |
| 2003/0088270 A1 | 5/2003 | Lubbers |
| 2003/0097150 A1 | 5/2003 | Fallin |
| 2003/0105489 A1 | 6/2003 | Eichhorn |
| 2003/0149447 A1 | 8/2003 | Morency |
| 2003/0158604 A1 | 8/2003 | Cauthen, III |
| 2003/0167072 A1 | 9/2003 | Oberlander |
| 2003/0203003 A1 | 10/2003 | Nelson |
| 2003/0204195 A1 | 10/2003 | Keane |
| 2003/0229361 A1 | 12/2003 | Jackson |
| 2003/0236550 A1 | 12/2003 | Peterson |

| Publication No. | Date | Name |
|---|---|---|
| 2003/0236551 A1 | 12/2003 | Peterson |
| 2004/0010275 A1 | 1/2004 | Jacobs |
| 2004/0010276 A1 | 1/2004 | Jacobs |
| 2004/0015187 A1 | 1/2004 | Lendlein |
| 2004/0024420 A1 | 2/2004 | Lubbers |
| 2004/0028655 A1 | 2/2004 | Nelson |
| 2004/0030354 A1 | 2/2004 | Leung |
| 2004/0039415 A1 | 2/2004 | Zamierowski |
| 2004/0059377 A1 | 3/2004 | Peterson |
| 2004/0059378 A1 | 3/2004 | Peterson |
| 2004/0060409 A1 | 4/2004 | Leung |
| 2004/0060410 A1 | 4/2004 | Leung |
| 2004/0068293 A1 | 4/2004 | Scalzo |
| 2004/0068294 A1 | 4/2004 | Scalzo |
| 2004/0088003 A1 | 5/2004 | Leung |
| 2004/0093023 A1 | 5/2004 | Allen |
| 2004/0093028 A1 | 5/2004 | Ruff |
| 2004/0098051 A1 | 5/2004 | Fallin |
| 2004/0106949 A1 | 6/2004 | Cohn |
| 2004/0138683 A1 | 7/2004 | Shelton |
| 2004/0153153 A1 | 8/2004 | Elson |
| 2004/0167572 A1 | 8/2004 | Roth |
| 2004/0167575 A1 | 8/2004 | Roby |
| 2004/0193191 A1 | 9/2004 | Starksen |
| 2004/0193217 A1 | 9/2004 | Lubbers |
| 2004/0193257 A1 | 9/2004 | Wu |
| 2004/0226427 A1 | 11/2004 | Trull |
| 2004/0237736 A1 | 12/2004 | Genova |
| 2004/0254609 A1 | 12/2004 | Esplin |
| 2004/0260340 A1 | 12/2004 | Jacobs |
| 2004/0265282 A1 | 12/2004 | Wright |
| 2004/0267309 A1 | 12/2004 | Garvin |
| 2005/0004601 A1 | 1/2005 | Kong |
| 2005/0004602 A1 | 1/2005 | Hart |
| 2005/0033324 A1 | 2/2005 | Phan |
| 2005/0033367 A1 | 2/2005 | Leung |
| 2005/0034431 A1 | 2/2005 | Dey |
| 2005/0038472 A1 | 2/2005 | Furst |
| 2005/0059984 A1 | 3/2005 | Chanduszko |
| 2005/0065533 A1 | 3/2005 | Magen |
| 2005/0070959 A1 | 3/2005 | Cichocki, Jr. |
| 2005/0080455 A1 | 4/2005 | Schmieding |
| 2005/0085857 A1 | 4/2005 | Peterson |
| 2005/0096698 A1 | 5/2005 | Lederman |
| 2005/0106211 A1 | 5/2005 | Nelson |
| 2005/0113936 A1 | 5/2005 | Brustad |
| 2005/0119694 A1 | 6/2005 | Jacobs |
| 2005/0125020 A1 | 6/2005 | Meade |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson |
| 2005/0149118 A1 | 7/2005 | Koyfman |
| 2005/0154255 A1 | 7/2005 | Jacobs |
| 2005/0171561 A1 | 8/2005 | Songer |
| 2005/0177190 A1 | 8/2005 | Zamierowski |
| 2005/0182444 A1 | 8/2005 | Peterson |
| 2005/0182445 A1 | 8/2005 | Zamierowski |
| 2005/0197699 A1 | 9/2005 | Jacobs |
| 2005/0199249 A1 | 9/2005 | Karram |
| 2005/0203576 A1 | 9/2005 | Sulamanidze |
| 2005/0209542 A1 | 9/2005 | Jacobs |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff |
| 2005/0267532 A1 | 12/2005 | Wu |
| 2005/0277984 A1 | 12/2005 | Long |
| 2005/0283246 A1 | 12/2005 | Cauthen |
| 2006/0020272 A1 | 1/2006 | Gildenberg |
| 2006/0030884 A1 | 2/2006 | Yeung et al. |
| 2006/0036266 A1 | 2/2006 | Sulamanidze |
| 2006/0058574 A1 | 3/2006 | Priewe |
| 2006/0058799 A1 | 3/2006 | Elson |
| 2006/0058844 A1 | 3/2006 | White |
| 2006/0064115 A1 | 3/2006 | Allen |
| 2006/0064116 A1 | 3/2006 | Allen |
| 2006/0064127 A1 | 3/2006 | Fallin |
| 2006/0079935 A1 | 4/2006 | Kolster |
| 2006/0085016 A1 | 4/2006 | Eremia |
| 2006/0089525 A1 | 4/2006 | Mamo |
| 2006/0089672 A1 | 4/2006 | Martinek |
| 2006/0111734 A1 | 5/2006 | Kaplan |
| 2006/0111742 A1 | 5/2006 | Kaplan |
| 2006/0122608 A1 | 6/2006 | Fallin |
| 2006/0135994 A1 | 6/2006 | Ruff |
| 2006/0135995 A1 | 6/2006 | Ruff |
| 2006/0142784 A1 | 6/2006 | Kontos |
| 2006/0193769 A1 | 8/2006 | Nelson |
| 2006/0194721 A1 | 8/2006 | Allen |
| 2006/0200062 A1 | 9/2006 | Saadat |
| 2006/0207612 A1 | 9/2006 | Jackson |
| 2006/0229671 A1 | 10/2006 | Steiner |
| 2006/0235445 A1 | 10/2006 | Birk |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin |
| 2006/0253126 A1 | 11/2006 | Bjerken |
| 2006/0257629 A1 | 11/2006 | Lendlein |
| 2006/0258938 A1 | 11/2006 | Hoffman |
| 2006/0272979 A1 | 12/2006 | Lubbers |
| 2006/0276808 A1 | 12/2006 | Arnal |
| 2006/0282099 A1 | 12/2006 | Stokes |
| 2006/0286289 A1 | 12/2006 | Prajapati |
| 2006/0287675 A1 | 12/2006 | Prajapati |
| 2006/0287676 A1 | 12/2006 | Prajapati |
| 2006/0293710 A1 | 12/2006 | Foerster |
| 2007/0005109 A1 | 1/2007 | Popadiuk |
| 2007/0005110 A1 | 1/2007 | Collier |
| 2007/0021779 A1 | 1/2007 | Garvin |
| 2007/0027475 A1 | 2/2007 | Pagedas |
| 2007/0038249 A1 | 2/2007 | Kolster |
| 2007/0065663 A1 | 3/2007 | Trull |
| 2007/0088391 A1 | 4/2007 | McAlexander |
| 2007/0135840 A1 | 6/2007 | Schmieding |
| 2007/0135843 A1 | 6/2007 | Burkhart |
| 2007/0151961 A1 | 7/2007 | Kleine |
| 2007/0156175 A1 | 7/2007 | Weadock |
| 2007/0167958 A1 | 7/2007 | Sulamanidze |
| 2007/0187861 A1 | 8/2007 | Genova |
| 2007/0208355 A1 | 9/2007 | Ruff |
| 2007/0208377 A1 | 9/2007 | Kaplan |
| 2007/0219587 A1 | 9/2007 | Accardo |
| 2007/0224237 A1 | 9/2007 | Hwang |
| 2007/0225642 A1 | 9/2007 | Houser |
| 2007/0225761 A1 | 9/2007 | Shetty |
| 2007/0227914 A1 | 10/2007 | Cerwin |
| 2007/0233188 A1 | 10/2007 | Hunt |
| 2007/0239206 A1 | 10/2007 | Shelton, IV |
| 2007/0257395 A1 | 11/2007 | Lindh |
| 2007/0282247 A1 | 12/2007 | Desai |
| 2008/0004603 A1 | 1/2008 | Larkin |
| 2008/0009838 A1 | 1/2008 | Schena |
| 2008/0009888 A1 | 1/2008 | Ewers |
| 2008/0009902 A1 | 1/2008 | Hunter |
| 2008/0027273 A1 | 1/2008 | Gutterman |
| 2008/0027486 A1 | 1/2008 | Jones |
| 2008/0046094 A1 | 2/2008 | Han |
| 2008/0058869 A1 | 3/2008 | Stopek |
| 2008/0066764 A1 | 3/2008 | Paraschac |
| 2008/0066765 A1 | 3/2008 | Paraschac |
| 2008/0066766 A1 | 3/2008 | Paraschac |
| 2008/0066767 A1 | 3/2008 | Paraschac |
| 2008/0077181 A1 | 3/2008 | Jones |
| 2008/0082113 A1 | 4/2008 | Bishop |
| 2008/0082129 A1 | 4/2008 | Jones |
| 2008/0086169 A1 | 4/2008 | Jones |
| 2008/0086170 A1 | 4/2008 | Jones |
| 2008/0109036 A1 | 5/2008 | Stopek |
| 2008/0132943 A1 | 6/2008 | Maiorino |
| 2008/0195147 A1 | 8/2008 | Stopek |
| 2008/0208358 A1 | 8/2008 | Bellamkonda |
| 2008/0215072 A1 | 9/2008 | Kelly |
| 2008/0221618 A1 | 9/2008 | Chen |
| 2008/0234731 A1 | 9/2008 | Leung |
| 2008/0248216 A1 | 10/2008 | Yeung |
| 2008/0262542 A1 | 10/2008 | Sulamanidze |

| | | | |
|---|---|---|---|
| 2008/0281338 A1 | 11/2008 | Wohlert | |
| 2008/0312688 A1 | 12/2008 | Nawrocki | |
| 2009/0012560 A1 | 1/2009 | Hunter | |
| 2009/0018577 A1* | 1/2009 | Leung et al. | 606/216 |
| 2009/0043336 A1 | 2/2009 | Yuan | |
| 2009/0076543 A1 | 3/2009 | Maiorino | |
| 2009/0099597 A1 | 4/2009 | Isse | |
| 2009/0107965 A1 | 4/2009 | D'Agostino | |
| 2009/0112259 A1 | 4/2009 | D'Agostino | |
| 2009/0200487 A1 | 8/2009 | Maiorino | |
| 2009/0210006 A1 | 8/2009 | Cohen | |
| 2009/0226500 A1 | 9/2009 | Avelar | |
| 2009/0248066 A1 | 10/2009 | Wilkie | |
| 2009/0248067 A1 | 10/2009 | Maiorino | |
| 2009/0248070 A1 | 10/2009 | Kosa | |
| 2009/0250356 A1 | 10/2009 | Kirsch | |
| 2009/0259233 A1 | 10/2009 | Bogart | |
| 2009/0259251 A1 | 10/2009 | Cohen | |
| 2009/0287245 A1 | 11/2009 | Ostrovsky | |
| 2009/0299407 A1 | 12/2009 | Yuan | |
| 2009/0299408 A1 | 12/2009 | Schuldt-Hempe | |
| 2009/0306710 A1 | 12/2009 | Lindh | |
| 2010/0023055 A1 | 1/2010 | Rousseau | |
| 2010/0057123 A1 | 3/2010 | D'Agostino | |
| 2010/0063540 A1 | 3/2010 | Maiorino | |
| 2010/0071833 A1 | 3/2010 | Maiorino | |
| 2010/0087855 A1 | 4/2010 | Leung | |
| 2010/0101707 A1 | 4/2010 | Maiorino | |
| 2010/0140115 A1 | 6/2010 | Kirsch | |
| 2010/0294103 A1 | 11/2010 | Genova | |
| 2010/0294104 A1 | 11/2010 | Genova | |
| 2010/0294105 A1 | 11/2010 | Genova | |
| 2010/0294106 A1 | 11/2010 | Genova | |
| 2010/0294107 A1 | 11/2010 | Genova | |
| 2010/0313723 A1 | 12/2010 | Genova | |
| 2010/0313729 A1 | 12/2010 | Genova | |
| 2010/0313730 A1 | 12/2010 | Genova | |

FOREIGN PATENT DOCUMENTS

| | | |
|---|---|---|
| CN | 2640420 | 9/2004 |
| DE | 1810800 | 6/1970 |
| DE | 3227984 | 7/1982 |
| DE | 4302895 | 8/1994 |
| DE | 196118891 | 4/1997 |
| DE | 198 33 703 A | 2/2000 |
| DE | 19833703 | 2/2002 |
| DE | 102005004317 | 6/2006 |
| EP | 0329787 | 8/1989 |
| EP | 0428253 | 5/1991 |
| EP | 0576337 | 12/1993 |
| EP | 0632999 | 1/1995 |
| EP | 0612504 | 11/1997 |
| EP | 0 826 337 A | 3/1998 |
| EP | 0826337 | 3/1998 |
| EP | 0 839 499 A | 5/1998 |
| EP | 0839499 | 5/1998 |
| EP | 0913123 | 5/1999 |
| EP | 0960600 | 12/1999 |
| EP | 1075843 | 2/2001 |
| FR | 2619129 | 2/1989 |
| FR | 2693108 | 1/1994 |
| GB | 267007 | 3/1927 |
| GB | 1091282 | 11/1967 |
| GB | 1 428 560 | 3/1976 |
| GB | 14228560 | 3/1976 |
| GB | 1506362 | 4/1978 |
| JP | 354116419 | 9/1979 |
| JP | 63288146 | 11/1988 |
| JP | 01113091 | 5/1989 |
| JP | 11332828 | 12/1999 |
| KR | 6013299 A | 2/2006 |
| NZ | 501224 | 3/2002 |
| NZ | 531262 | 6/2002 |
| RU | 1745214 | 7/1992 |
| RU | 1752358 | 8/1992 |
| RU | 2139690 | 10/1999 |
| WO | WO9606565 | 3/1996 |
| WO | WO9852473 | 11/1998 |
| WO | WO9921488 | 5/1999 |
| WO | WO9905477 | 11/1999 |
| WO | WO0051658 | 9/2000 |
| WO | WO03001979 | 1/2003 |
| WO | WO 03/017850 | 3/2003 |
| WO | WO03017850 | 3/2003 |
| WO | WO03045255 | 6/2003 |
| WO | WO03103733 | 12/2003 |
| WO | WO03103972 | 12/2003 |
| WO | WO2004014236 | 2/2004 |
| WO | WO2004030520 | 4/2004 |
| WO | WO2004030704 | 4/2004 |
| WO | WO2004030705 | 4/2004 |
| WO | WO2004112853 | 12/2004 |
| WO | WO2006005144 | 1/2006 |
| WO | WO2006061868 | 6/2006 |
| WO | WO2006082060 | 8/2006 |
| WO | WO2006099703 | 9/2006 |
| WO | WO2007053812 | 5/2007 |
| WO | WO2007133103 | 11/2007 |
| WO | WO2007145614 | 12/2007 |
| WO | WO2009068252 | 6/2009 |
| WO | WO2009087105 | 7/2009 |
| WO | WO2010052007 | 5/2010 |

OTHER PUBLICATIONS

International Search Report for PCT/US2008/060127 dated Sep. 23, 2008, 5 pages.

International Search Report for PCT/US2008/0064921 dated Nov. 19, 2008, 3 pages.

International Search Report for PCT/US2008/075849 dated Mar. 18, 2009, 4 pages.

Singapore Search Report for Singapore Patent Application No. 200702625-5 dated Nov. 26, 2008, 7 pages.

Singapore Search Report for Singapore Patent Application No. 200702350-0 dated Nov. 26, 2008, 6 pages.

Singapore Search Report for Singapore Patent Application No. 200703688-2 dated Nov. 26, 2008, 7 pages.

European Search Report for EP07015905.8 dated Oct. 23, 2007, 2 pages.

European Search Report for EP10000629.5 dated Mar. 10, 2010, 4 pages.

European Search Report for EP10011871.0 dated Dec. 3, 2010, 2 pages.

European Search Report for EP10011868.6 dated Dec. 6, 2010, 2 pages.

European Search Report for EP10186592.1 dated Jan. 19, 2011, 2 pages.

Mason, M.L., "Primary and secondary tendon suture. A discussion of the significance of technique in tendon surgery", Surg Gynecol Obstet 70 (1940).

McKee, G.K., "Metal anastomosis tubes in tendon suture", The Lancet, May 26, 1945, 659-660.

Mansberger, et al., "A New Type Pull-Out Wire for Tendon Surgery: A Preliminary Report", Department of Surgery, University Hospital and University of Maryland School of Medicine, Baltimore, Maryland, Received for Publication May 10, 1951, pp. 119-121.

Jennings et al., "A new technique in primary tendon repair", Surg Gynecol Obstet Nov. 1952;95(5):597-600.

Bunnell, S., "Gig pull-out suture for tendons", J Bone Joint Surg Am. Jul. 1954;36-A(4):850-1.

Verdan, Claude, "Primary Repair of Flexor Tendons", Journal of Bone and Joint Surgery Jun. 1960; 42(4):647-657.

Potenza, Austin, "Tendon Healing Within the Flexor Digital Sheath in the Dog: An Experimental Study", Journal of Bone & Joint Surgery Jan. 1962; 44A(1):49-64.

Pulvertaft, "Suture Materials and Tendon Junctures", American Journal of Surgery Mar. 1965; 109:346-352.

Buncke, Jr., H.J. et al., "The suture repair of one-millimeter vessels, micro-vascular surgery", Report of First Conference; Oct. 6-7, 1966; pp. 24-35 (esp. p. 34), USA.

McKenzie, A.R., "An Experimental Multiple Barbed Suture for the Long Flexor Tendons of the Palm and Fingers", Journal of Bone and Joint Surgery 1967; 49B(3): 440-447.

Zoltan, Janos, "Cicatrix Optimia: Techniques for Ideal Wound Healing", English language edition University Park Press, Baltimore, 1977:Chapter 3; pp. 54-55.

Han, Hongtao et al., "Mating and Piercing Micromechanical Structures for Surface Bonding Applications", Proceedings of the 1991 Micro Electro Mechanical Systems (MEMS >91), an Investigation of Micro Structures, Sensors, Actuators, Machines and Robots, Feb. 1991, pp. 253-258.

Malina, Martin et al., "Endovascular AAA Exclusion: Will Stents With Hooks and Barbs Prevent Stent-Graft Migration", Journal Endovascular Surgery 1998(5): 310-317.

Boenisch, U.W. et al., "Pull-our strength and stiffness of meniscal repair using absorbable arrows or Ti-Cron vertical and horizontal loop sutures", American Journal of Sports Medicine, Sep.-Oct. 1999, pp. 626-631, vol. 27, Issue 5.

Sulamanidze, MD, M.A., et al., "Management of Facial Rhytids by Subcutaneous Soft Tissue Dissection", International Journal of Cosmetic Surgery and Aesthetic Dermatology, vol. 2(4), 2000, pp. 255-259.

Rofin-Baasel, "Laser Marking on Plastic Materials", 2001.RB50.0, Rofin-Baasel Inc. 2001, 2 pages.

Semenov, G. M. et al., "Surgical Suture", 2001, pp. 12-13 and 92-98, Piter, Saint Petersburg.

Sulamanidze, M.A. et al., "Facial lifting with Aptos threads", International Journal of Cosmetic Surgery and Aesthetic Dermatology, 2001, pp. 1-8, No. 4.

Dattillo, Jr., Philip Paul, "Medical Textile: Application of an Absorbable Barbed Bi-Directional Surgical Suture", Journal of Textile and Apparel, Technology and Management, vol. 2(2), Spring 2002, pp. 1-5.

Lendlein, Andreas et al., "Biodegradable, Elastic Shape-Memory Polymers for Potential Biomedical Applications", Science vol. 296; May 31, 2002, pp. 1673-1676.

Leung, J. et al., "Barbed, Bi-directional Medical Sutures: Biomechanical Properties and Wound Closure Efficacy Study", 2002 Society for Biomaterials 28$^{th}$ Annual Meeting Transactions, 1 page.

Sulamanidze, MD, M.A., et al., "Removal of Facial Soft Tissue Ptosis with Special Threads", Dermatol Surg 2002; 28; pp. 367-371.

Lendlein, Andreas et al., "Shape-Memory Polymers", Angew, Chem. Int. Ed. 2002, 41, 2034-2057.

Sulamanidze, MD, M.A., et al., "Clinical aspects of bloodless facelift using APTOS filaments", A.V. Vishnevsky Institute of Surgery, Bol=shaya Serpukhovskaya ul., 27, 113811 Moscow, Russia, (2002):24-34.

Sulamanidze, MD, M.A., et al., "Morphological foundations of facelift using APTOS filaments", Bolshaya Serpukhovskaya ul., 27, 113811 Moscow, Russia, (2002): 19-26.

Dattillo, Jr., Philip Paul, et al., "Tissue Holding Performance of Knotless Absorbable Sutures", 2003 Society for Biomaterials 29$^{th}$ Annual Meeting Transactions, p. 101.

Ingle, Nilesh P. et al., "Mechanical Performance and Finite Element Analysis of Bi-directional Barbed Sutures", Master of Science in Textile Technology & Management at North Carolina State University Aug. 2003, 126 pages.

Kuniholm, Jonathan Fairbank, et al., "Automated Knot Tying for Fixation in Minimally Invasive, Robot Assisted Cardiac Surgery", Master of Science in Mechanical & Aerospace Engineering at North Carolina State University May 2003, 71 pages.

Leung, J. et al., "Barbed Bi-directional Surgical Sutures: In Vivo Strength and Histopathology Evaluations", 2003 Society for Biomaterials 29$^{th}$ Annual Meeting Transactions, p. 100.

Li, Yang Yang, et al., "Polymer Replicas of Photonic Porous Silicon for Sensing and Drug Delivery Applications", Science vol. 299; Mar. 28, 2003, pp. 2045-2047.

Leung, Jeffrey C. et al., "Barbed, Bi-Directional Surgical Sutures", International Conference & Exhibition on Healthcare & Medical Textiles, Jul. 8-9, 2003; 1-8.

Szarmach, Robin et al., "An Expanded Surgical Suture and Needle Evaulation and Selection Program by a Healthcare Resource Management Group Purchasing Organization", Journal of Long-Term Effects of Medical Implants 2003; 13(3); 155-170.

Ingle, Nilesh P et al., "Barbed Suture Anchoring Strength: Applicability to Dissimilar Polymeric Materials", College of Textiles, North Carolina State University, 7$^{th}$ World Biomaterials Congress 2004, 1 page.

Leung, J. et al., "Performance Enhancement of a Knotless Suture via Barb Geometry Modifications", 7$^{th}$ World Biomaterials Congress 2004, 1 page.

Wu, Woffles, "Barbed Sutures in Facial Rejuvenation", Aesthetic Surgery Journal 2004(24): 582-587.

Quill Medical, Inc., "Quill Medical's Novel-Self-Anchoring Surgical Suture Approved for Sale in Europe", Press Release; Research Triangle Park, N.C., May 10, 2004, 1 page.

Buckley, Patrick R., "Actuation of Shape Memory Polymer using Magnetic Fields for Applications in Medical Devices", Master of Science in Mechanical Engineering at the Massachusetts Institute of Technology Jun. 2003, 144 pgs.

Quill Medical, Inc., "Barbed sutures, wrinkle filters give patients more innovative, non-surgical options", Press Release of Program presented at American Society of Plastic Surgeons annual scientific meeting; Philadelphia, Oct. 9, 2004, 3 pages.

Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.

Surgical Specialties Corporation, "Wound Closure Catalog"; Summer 2005, 5 pages.

Rodeheaver, G.T. et al., "Barbed Sutures for Wound Closure: In Vivo Wound Security, Tissue Compatibility and Cosmesis Measurements", Society for Biomaterials 30$^{th}$ Annual Meeting Transactions, 2005, 2 pages.

Belkas, J. S. et al., "Peripheral nerve regeneration through a synthetic hydrogel nerve tube", Restorative Neurology and Neuroscience 23 (2005) 19-29.

Ingle, Nilesh P et al., "Testing the Tissue-holding Capacity of Barbed Sutures", College of Textiles, North Carolina State University, Fiber Science, the Next Generation Oct. 17-19, 2005, New Jersey Institute of Technology, Newark, NJ, 4 pages.

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

De Persia, Raúl et al., "Mechanics of Biomaterials: Sutures After the Surgery", Applications of Engineering Mechanics in Medicine, GED-University of Puerto Rico, Mayaguez May 2005, p. F1-F27.

Scherman, Peter et al., "Sutures as longitudinal guides for the repair of nerve defects-Influence of suture numbers and reconstruction of nerve bifurcations", Restorative Neurology and Neuroscience 23 (2005) 79-85.

Sulamanidze, MD, M.A., et al., "Soft tissue lifting in the mid-face: old philosophy, new approach-internal stitching technique (APTOS Needle)", Plastic and Aesthetic Surgery Clinic Total Sharm, Moscow, Russia, (2005):15-29.

Bacci, Pier Antonio, "Chirurgia Estetica Mini Invasiva Con Fili Di Sostegno", Collana di Arti, Pensiero e Scienza; Minelli Editore—2006; 54 pages.

Bellin, I. et al., "Polymeric triple-shape materials", Proceedings of the National Academy of Sciences of the United States of America Nov. 28, 2006; 2103(48):18043-18047.

Delorenzi, C.L., "Barbed Sutures: Rationale and Technique", Aesthetic Surg J. Mar. 2006 26(2): 223-229.

Gross, Alex, "Physician perspective on thread lifts", Dermatology Times Feb. 2006 27(2): 2 pages.

Khademhosseini, Ali et al., "Nanobiotechnology Drug Delivery and Tissue Engineering", Chemical Engineering Progress 102:38-42 (2006).

Murtha et al., "Evaluation of a Novel Technique for Wound Closure Using a Barbed Suture", Journal of the American Society of Plastic Surgeons 2006; 117(6); 1769-1780.

Ruff, Gregory, "Technique and Uses for Absorbable Barbed Sutures", Aesthetic Surgery Journal Sep./Oct. 2006; 26:620-628.

Behl, Marc et al., "Shape-Memory Polymers", Materials Today Apr. 2007; 10(4); 20-28.

Kaminer, M. et al., "ContourLift™: A New Method of Minimally Invasive Facial Rejuvenation", Cosmetic Dermatology Jan. 2007; 20(1): 29-35.

Kelch et al., "Shape-memory Polymer Networks from Olio[(0-hydroxycaproate)-co-glycolate]dimethacrylates and Butyl Acrylate with Adjustable Hydrolytic Degradation Rate", Biomacromolecules 2007;8(3):1018-1027.

Maitland et al., "Prototype laser-activated shape memory polymer foam device for embolic treatment of aneurysms", Journal of Biomedical Optics May/Jun. 2007;12(3): pp. 030504-1 to 030504-3.

Moran et al., "Bidirectional-Barbed Sutured Knotless Running Anastomosis v Classic van Velthovan in a Model System", Journal of Endourology Oct. 2007; 21(10); 1175-1177.

Mullner, "Metal Foam Has a Good Memory", Dec. 18, 2007 Original story at <http://www.physorg.com/news117214996.html>.

Paul, Malcolm D. and Rui Avelar, "Quill™ SRS Techniques & Procedures a Novel Approach to Soft Tissue Approximation", Canada, Angiotech Pharmaceuticals, Inc., First Edition [8]2007: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Second Edition [8]2008: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, [8] 2007-2009: 27 pages.

Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, [8] 2007-2010: 27 pages.

Dahlin, Lars, "Techniques of Peripheral Nerve Repair", Scandinavian Journal of Surgery 97: 310-316, 2008.

Madduri, Srinivas, et al., "Neurotrophic factors release from nerve conduits for peripheral axonal regeneration", European Cells and Materials vol. 16; Suppl. 1 (2008), p. 14.

Nie, Zhihong and Kumacheva, Eugenia, "Patterning surfaces with functional polymers", Nature Materials vol. 7(2008): 277-290.

Paul, Malcolm D., "Using Barbed Sutures in Open/Subperiosteal Midface Lifting", Aesthetic Surgery Journal 2006(26): 725-732.

Richert, Ludovic, et al., "Surface Nanopatterning to Control Cell Growth", Advanced Materials 2008(15): 1-5.

Tan Ee Lim et al., "A wireless, passive strain sensor based on the harmonic response of magnetically soft materials", Smart Materials and Structures 17 (2008): pp. 1-6.

Villa, Mark T. et al., "Barbed Sutures: A Review of Literature", Plastic and Reconstructive Surgery; Mar. 2008; vol. 121, No. 3; pp. 102e-108e.

Demyttenaere, Sebastian V. et al., "Barbed Suture for Gastrointestinal Closure: A Randomized Control Trial", Surgical Innovation; vol. 16, No. 3; Sep. 2009; pp. 237-242.

Einarsson, Jon I. et al., "Barbed Suture, now in the toolbox of minimally invasive gyn surgery", OBG Management; vol. 21, No. 9; Sep. 2009; pp. 39-41.

Paul, Malcolm D., "Bidirectional Barbed Sutures for Wound Closure: Evoluation and Applications", Journal of the American College of Certified Wound Specialists (2009) 1, 51-57.

Sulamanidze, Marlen et al., "APTOS Suture Lifting Methods: 10 Years of Experience", Clin Plastic Surg 36 (2009); pp. 281-306.

Ingle, N. P. et al., "Optimizing the tissue anchoring performance of barbed sutures in skin and tendon tissues", Journal of Biomechanics 43 (2010); pp. 302-309.

International Search Report for PCT/US2002/027525 dated Dec. 9, 2002, 3 pages.

European Search Report for EP107006258.3 dated May 4, 2007, 4 pages.

International Search Report for PCT/US2004/014962 dated Feb. 24, 2005, 6 pages.

US 6,447,535, 09/2002, Jacobs (withdrawn)
US 6,503,260, 01/2003, Schaller (withdrawn)

* cited by examiner

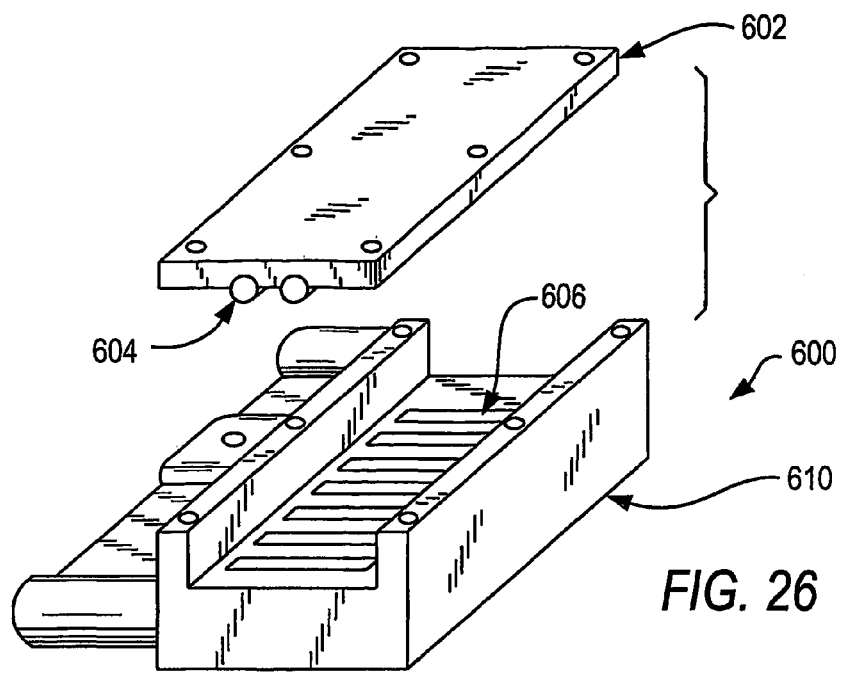
FIG. 26
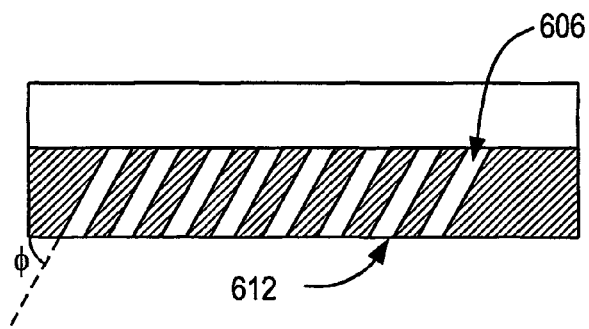
FIG. 27
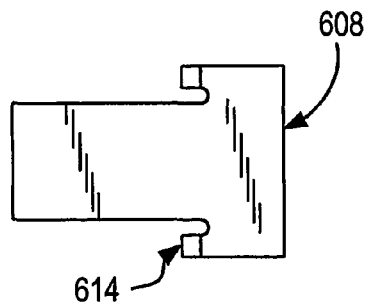
FIG. 28
FIG. 29
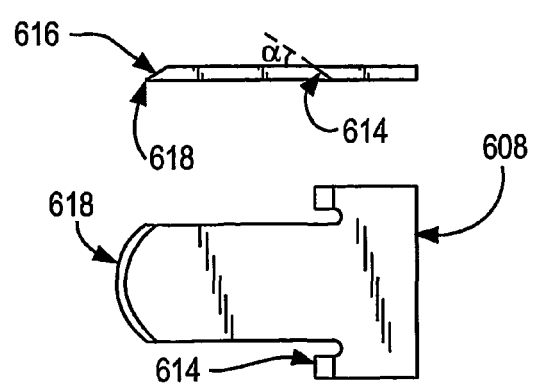
FIG. 30

APPARATUS FOR FORMING BARBS ON A SUTURE

This application is a 371 of PCT/US2004/014962 filed on May 13, 2004, published on Nov. 25, 2004 under publication number WO 2004/100801 A2 which claims priority benefits from U.S. patent application Ser. No. 10/437,144 filed May 13, 2003.

BACKGROUND OF THE INVENTION

1. Field of the Invention

The invention relates to an apparatus for forming barbs on a filament and the component parts of the apparatus.

2. Description of the Prior Art

In the prior art, it is well known that surgical and traumatic wounds are typically closed with a filament introduced into the tissue by a needle attached to one end. Closure of the wound and holding tissues together supports healing and re-growth. What is typically used for this procedure is known as a suture.

A barbed suture is a one-way suture which allows passage of a needle-drawn suture in one direction through tissue, but not in the opposite direction. A barbed suture is generally an elongated body having a pointed leading end and a plurality of axially and circumferentially spaced barbs on the exterior surface of the elongated body.

In closing a wound with a barbed suture, the suture is passed through tissue at each of the opposed sides of a wound. Suture pairs are formed in which trailing ends of sutures are positioned generally in alignment at opposite sides of the wound. On insertion of each suture, the needle is pushed to extend out of the tissue at a point laterally remote from the wound, then the needle is pulled out to draw the suture to the desired position. The suture may then be severed from the needle or inserted again. (Note that methods of using barbed sutures are disclosed in copending U.S. patent application Ser. No. 09/943,733, "Method of Forming Barbs on a Suture and Apparatus for Performing Same" the disclosures of which is incorporated herein by reference.) These methods are also described in International Patent Application, PCT/US02/27525. One advantage of using barbed sutures is that there is an ability to put tension in the tissue with the result of less slippage of the suture in the wound. Another advantage is that barbed sutures do not require tying as in prior art suturing methods. The number of suture pairs is selected in accordance with the size of the wound and the strength required to hold the wound closed. Although tissue anchoring is easier with a very pointed barb and a relatively skinny tip, better tissue holding results are obtained with a fuller tip barb.

In some circumstances of tissue repair, a random configuration of barbs on the exterior of the suture is preferred. With as many barb angles as possible, superior wound holding may be achieved. However, in other circumstances where the wound or tissue repair needed is small, a small suture is preferable. A thin suture may require a reduced number of barbs on the exterior of the suture.

In other circumstances the use of two-way barbed suture is preferable. A two-way barbed suture is one that has barbs permitting passing of the suture in one direction over a portion of the suture and barbs permitting passing of the suture in a second direction over another portion of the suture. Such an arrangement permits the passage of the suture through the tissue until the second set of barbs abut the tissue. Because the first set of barbs cannot be passed backward through the tissue and the second set of barbs cannot pass through the tissue, a firm closing stitch can be easily accomplished.

Additional methods of cutting barbs on a suture filament have been proposed (see e.g. U.S. Pat. No. 5,931,855 to Buncke).

It is seen from the foregoing that there is a need for an apparatus for cutting barbs in two directions on the exterior of sutures with a minimum of difficulty and in a precise, reliable and relatively economic fashion so as to allow for the wide spread commercialization of such sutures. Such an apparatus should also be able to vary the size of the barbs, their location and depth to allow for variation thereof and virtuality of their application. The apparatus should be able to cut a plurality of barbs positioned depending on the number of barbs needed. The configuration of the apparatus should also be variable depending upon, among other things, the type barbs being cut and the type of filament material, both of which relate to the type tissue being repaired. The apparatus should further be comprised of a series of components each of which facilitates the cutting of the barbs, these components being variable in configuration depending upon the desired features of the barbs to be cut.

OBJECTS OF THE INVENTION

It is therefore an object of the present invention to provide an apparatus for cutting barbs into a filament. The apparatus includes a filament supply, an in-feed collet for holding one end of a filament threaded therethrough, and an out-feed collet for holding a second end of a filament threaded therethrough. The apparatus also includes a holder positioned between the in-feed and out-feed collets for holding a filament suspended between them and a cutting assembly for cutting barbs in the filament tensioned between the in-feed and out feed collets. The apparatus may further include a tensioner for tensioning the filament held between the in-feed and out-feed collets, and a cutter for cutting a filament to a desired length to form a suture after barbs have been cut into the filament.

The cutting assembly may be formed of a first directional feed motor for moving a first cutter, a second directional feed motor for moving a second cutter, and a third directional feed motor for moving a grasping tool. The first and second cutters cut barbs into a filament and the grasping tool advances the filament after cutting of the barbs. The directional feed motors may comprise a series of feed motors that permit the independent motion of the cutters along the vertical, longitudinal, and perpendicular directions relative to the filament. The directional feed motors may move in varying degrees of motion relative to the other directional feed motors to enable the barbs to be cut in various lengths, depths, and shapes.

The present invention also relates to an apparatus for cutting barbs into sutures having a first directional feed motor for moving a first cutter, a second directional feed motor for moving a second cutter, and a third directional feed motor for moving a grasping tool, wherein the first and second cutters cut barbs into a filament and the grasping tool advances the filament after cutting of the barbs. The apparatus may also include a severing blade for severing the filament after advancement to form a suture.

The present invention further relates to a holder for securing a suture in preparation for the cutting of barbs. The holder includes a bed, having a channel arranged in the bed, and a plurality of orifices arranged along the channel. Each orifice has a first end exposed in the channel and a second end connected to a suction. A suction applied to the second end creates a vacuum for securing a suture placed over the orifices.

Still further, the present invention relates to a collet for holding a suture in place relative to its longitudinal axis during the cutting of barbs. The collet includes a chuck support and a chuck with a variably adjustable aperture. The chuck includes a plurality of jaws, whereby movement of the jaws adjusts the aperture of the chuck. The chuck may have two, three, or more jaws. The chuck may be configured to impart a variable filament retention force depending upon the characteristics of the filament be used. This variable filament retention force prevents damage to the filament. In a two jawed configuration, it may be preferable that a face of the jaw contacting the suture be concave. The chuck may further be rotatable about a longitudinal axis of a suture to impart twist to the suture. It may be preferable that the collet rotate in both a first and second direction. Further, the collet may be formed of materials that do not impart contaminants onto the filament.

Further still, the present invention relates to an apparatus for cutting barbs into sutures having a suture material supply, for feeding suture material to at least one collet and a tensioner. The tensioner includes at least one fixed pulley and at least one movable biased pulley, wherein the movable biased pulley imparts a force on the suture material tensioning a section of suture material held by the at least one collet. The tensioner may be adjustable to provide a variable but uniform amount of tension to a variety of filament types.

Yet another aspect of the present invention relates to an apparatus for cutting barbs into sutures having at least one collet and at least one biased tensioner. The biased tensioner allows the collet to move in a first direction as a suture held in a chuck housed in the collet is twisted. The biased tensioner moves the collet in a second direction as the suture is untwisted. The movement of the collet permits the cutting of the suture either before or after twisting and insures that the suture receives no more than a specified tension.

The present invention still further relates to a cutter for use in an apparatus for cutting barbs into sutures. The cutter includes a first edge which has a sharply honed edge for cutting a barb into a suture to a specified depth and in a specified direction. The cutter may also include a second edge which is blunted and roughened to impart a roughened texture to a surface of the barb cut into the suture, e.g. a serrated or corrugated underside. Alternatively, cutting blades with ends that are arcuate can create an arcuate shape at the base of the barb so as to reduce the sheering stress focused at the vertex of the barb.

In a further embodiment, the present invention relates to an apparatus for cutting barbs into a suture having a filament supply, at least one collet for holding a filament, a cutting bed for resting a filament thereon, and a cutting assembly for cutting barbs in the filament.

In yet a further embodiment the present invention relates to a method of forming a barbed suture comprising the steps of first threading a filament from a filament supply through a filament tensioner and through a first and second collet. Next the first and second collets are closed, and at least one of them is rotated in a first direction to twist the filament. Barbs are then cut into the filament. The filament is then untwisted and the collets are opened. The filament is then advanced with the use of a grasping tool, and the collets are again closed. Then the filament is severed to form a suture.

In yet a further embodiment the present invention relates to a method of forming a barbed suture comprising the steps of first threading a filament from a filament supply through a filament tensioner and through a first and second collet. Next the first and second collets are closed, and barbs are then cut into the filament. At least one of them is then rotated in a first direction to twist the filament. The filament is then either released or partially untwisted imparting a twisted conformation to the suture. The collets are opened and the filament is then advanced with the use of a grasping tool, and the collets are again closed. Then the filament is severed to form a suture.

These and other objects and characteristics of the present invention will become apparent from the further disclosure to be made in the detailed description given below.

FIG., 13, depicts a close-up perspective view of the out-feed collet and the cutter.

Figure 14:
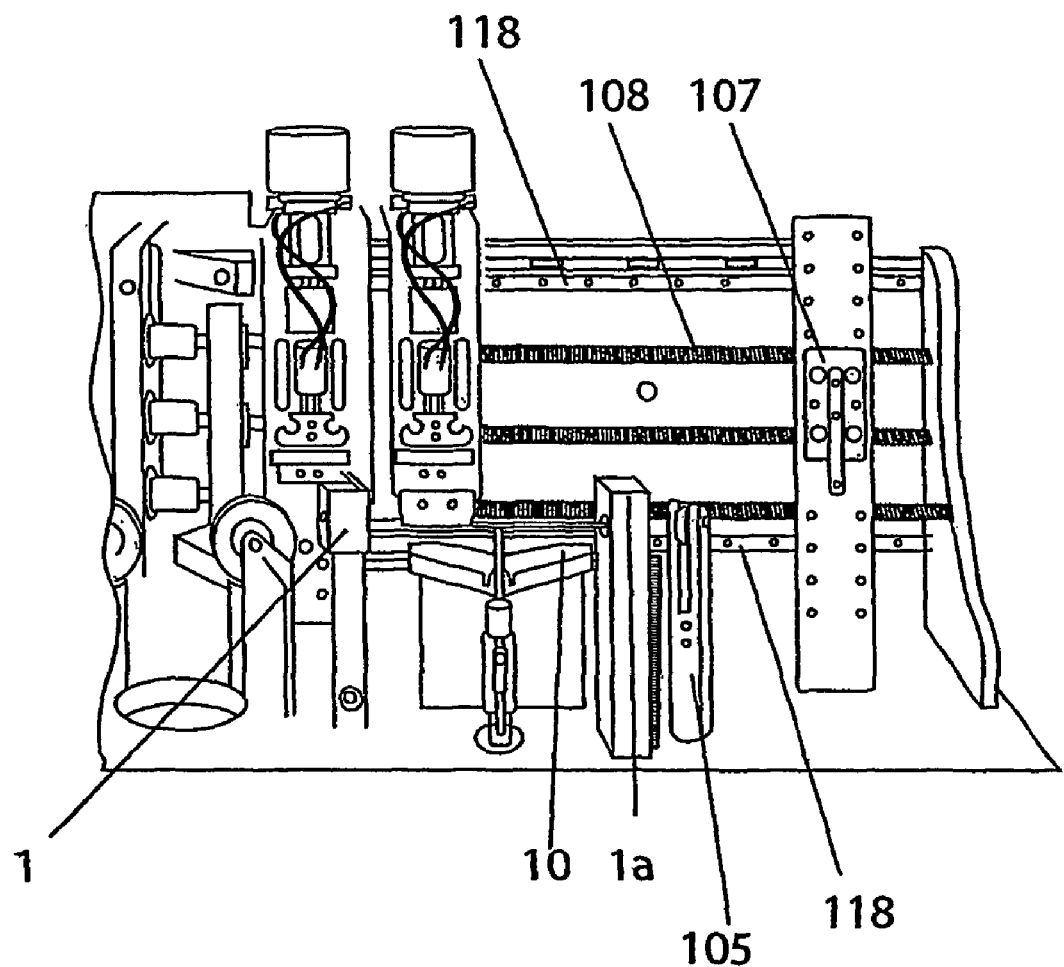

FIG. 14, depicts a close up view of the cutting assembly, and the in-feed and out-feed collets.

Figure 15:
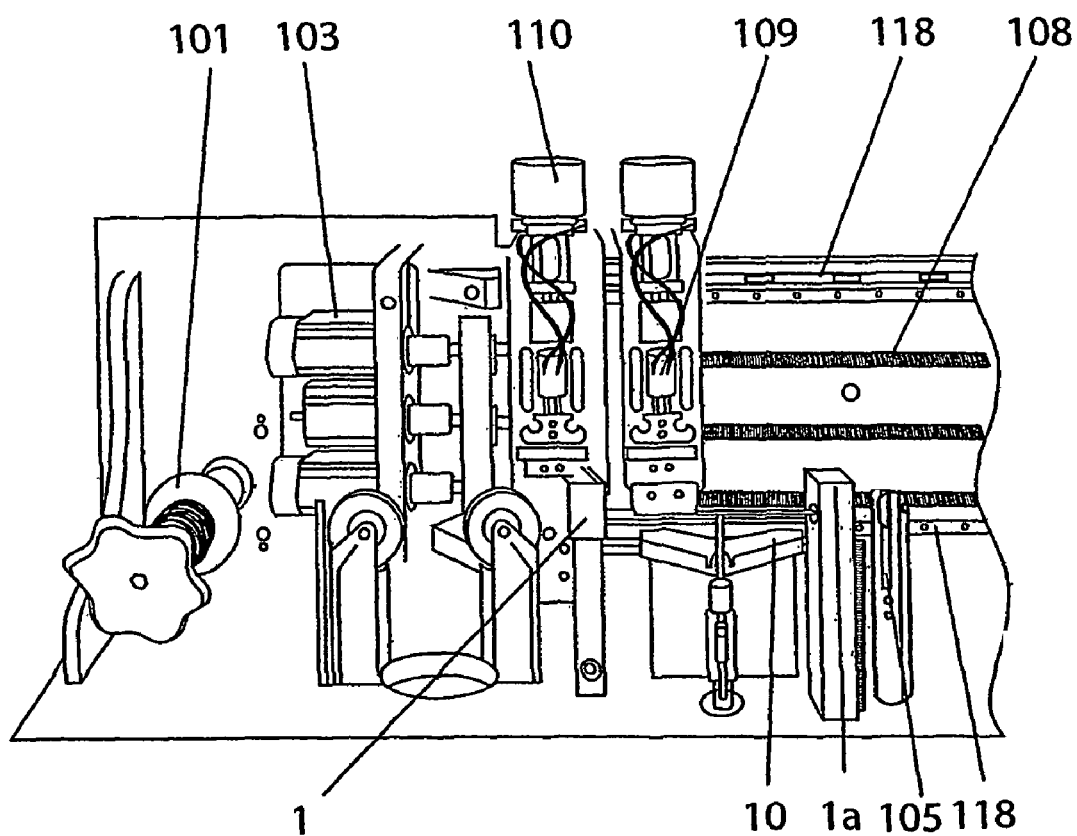

FIG. 15, depicts a close up view of the apparatus.

Figure 16:
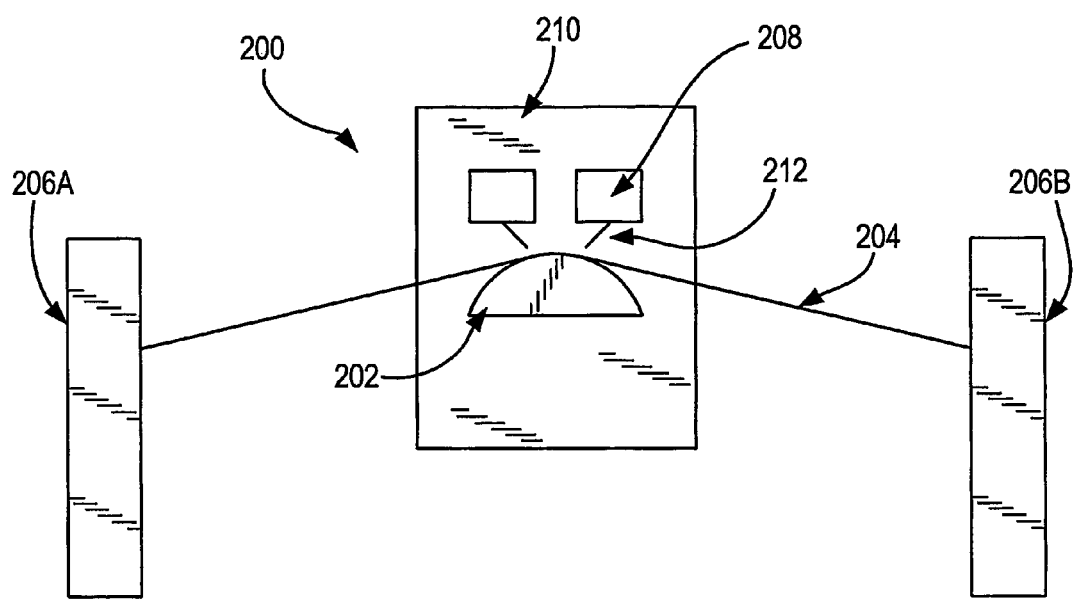

FIG. 16, depicts a suture vise according to a further embodiment of the present invention.

Figure 17:
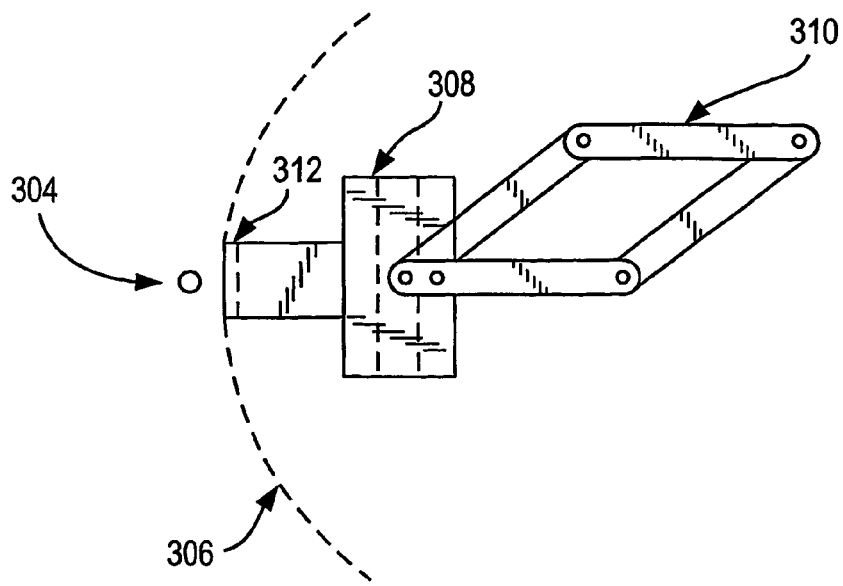
Figure 18:
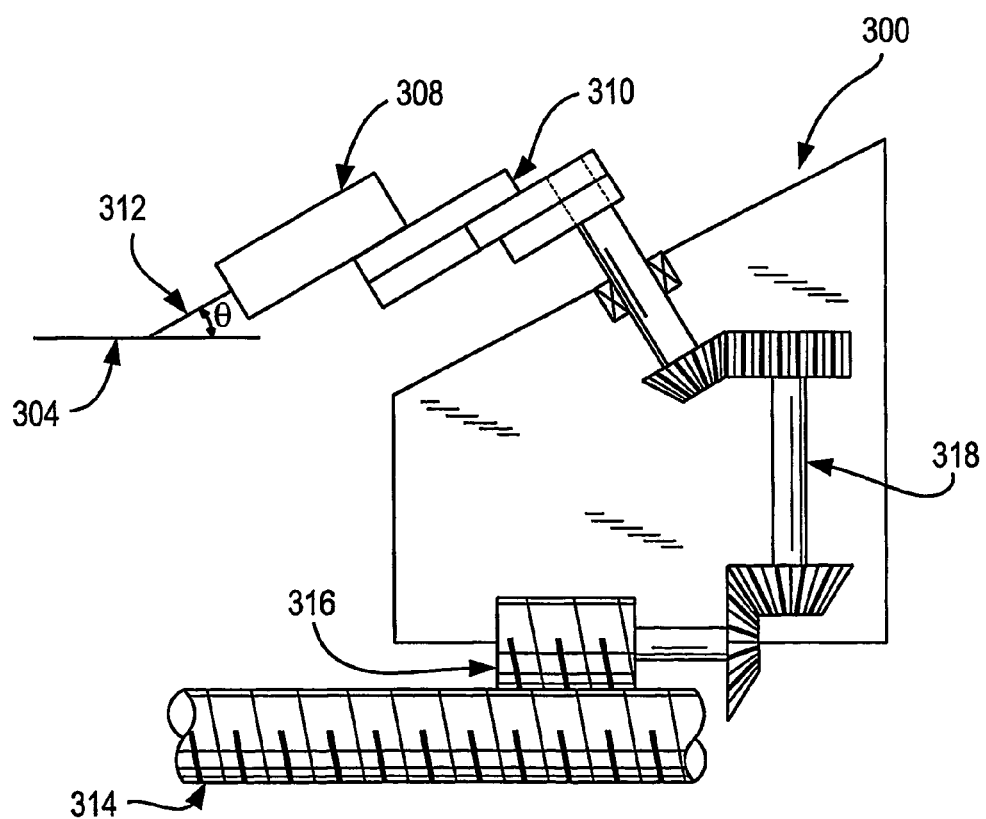

FIG. 17, depicts a 4-bar linkage system according to one embodiment of the present invention;

FIG. 18, depicts a 4-bar linkage barb cutter according to the present invention.

Figure 19:
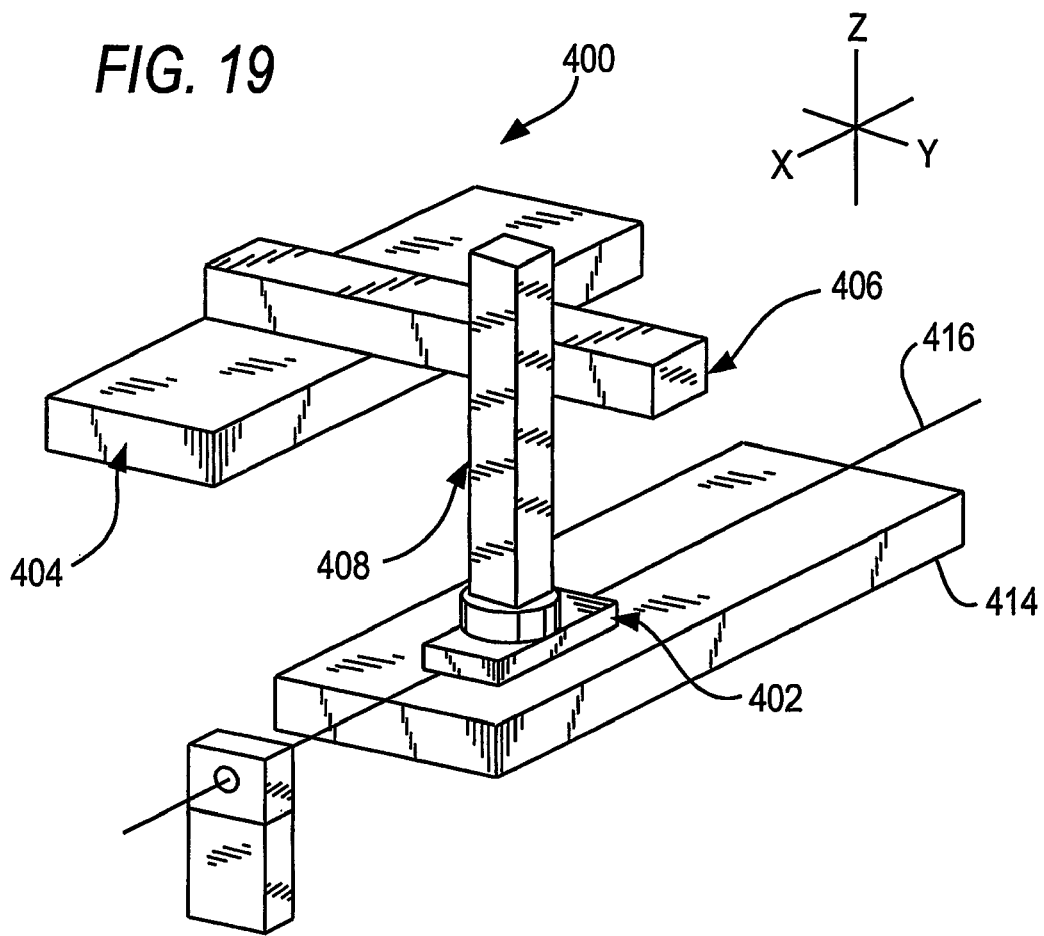

FIG. 19, depicts a 3-axis robot according to the present invention.

Figure 20:
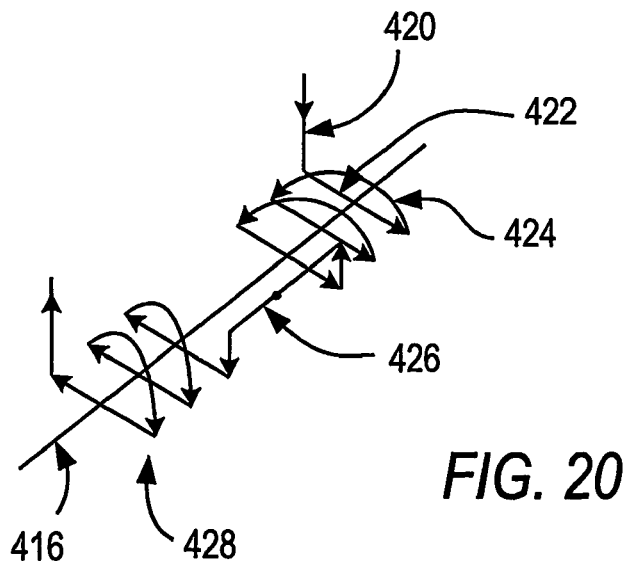

FIG. 20, depicts an exemplary movement series of a 3-axis robot according to the present invention.

Figure 21:
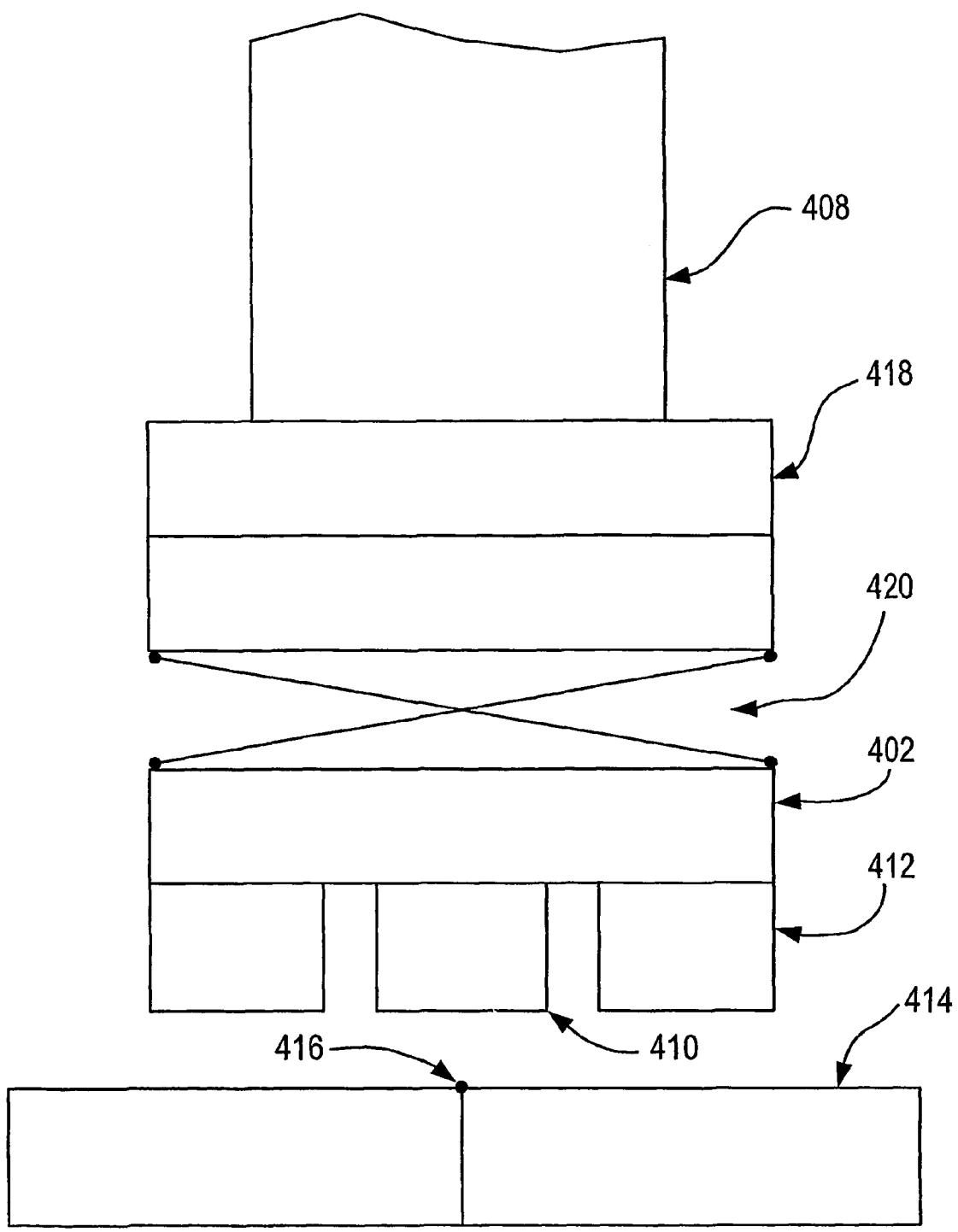

FIG. 21, depicts a close up view of a cutter head according to the present invention.

Figure 22:
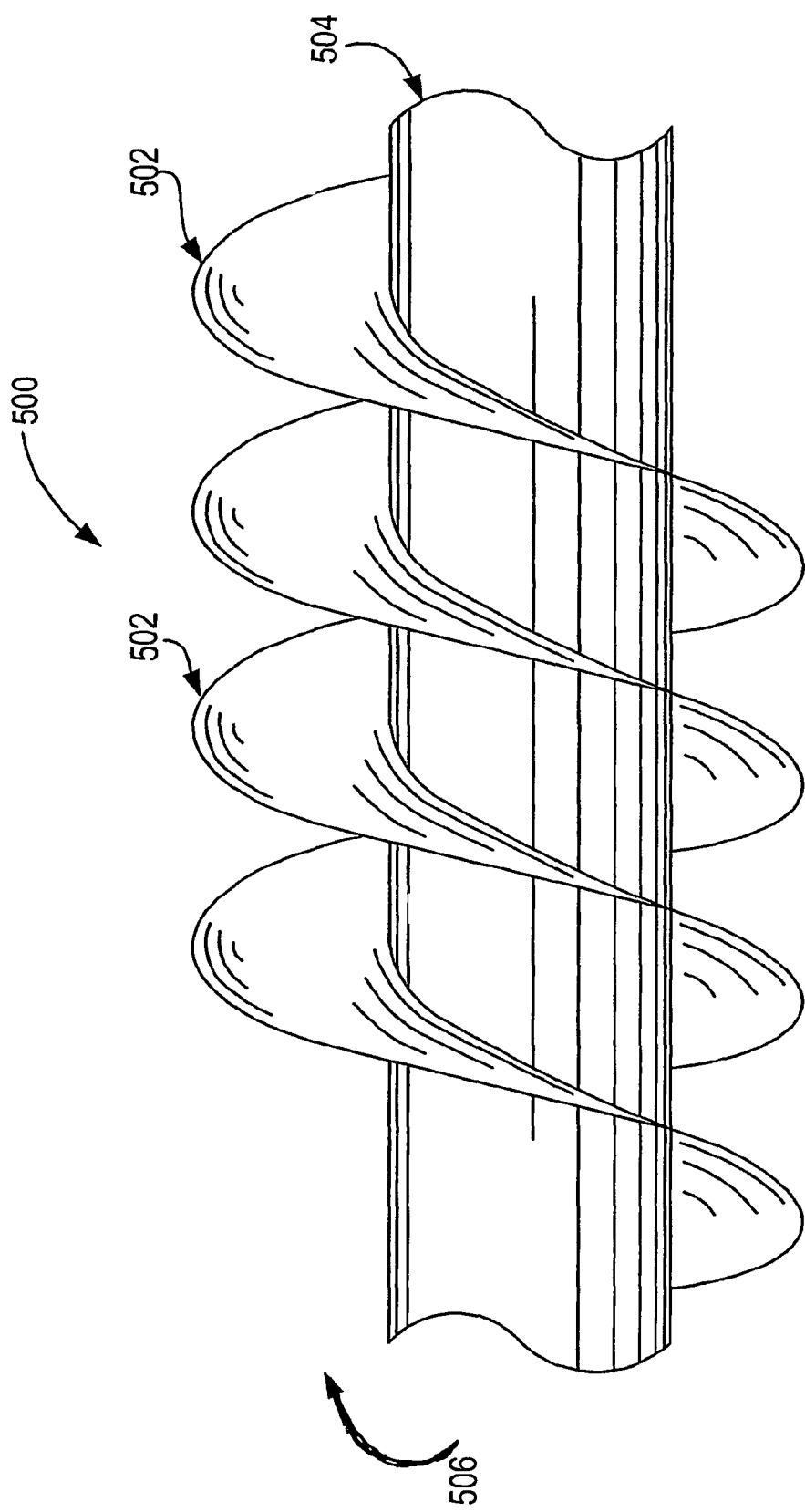

FIG. 22, depicts a cutter mechanism according to the present invention.

Figure 23:
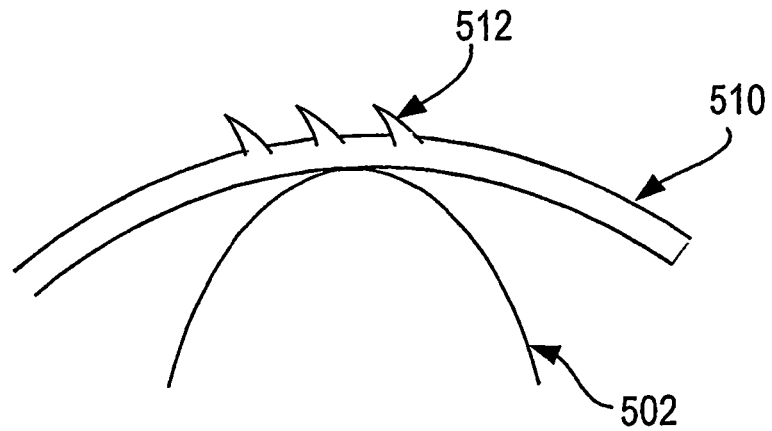
Figure 24:
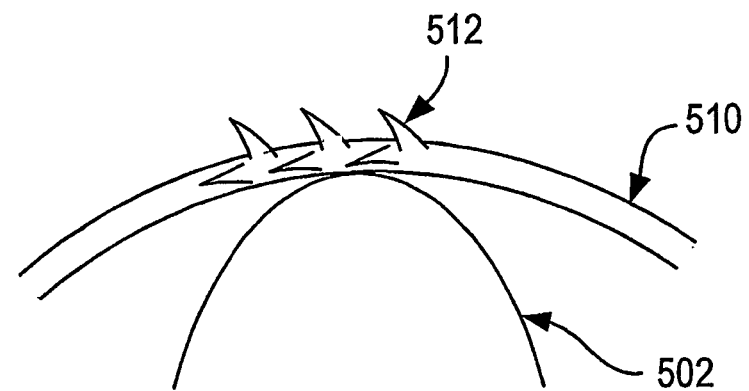
Figure 25:
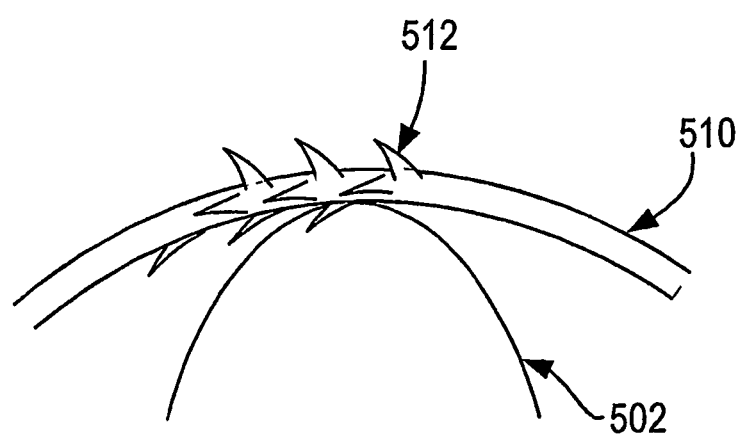

FIGS. 23-25, depict the formation of barbs on a suture using the cutter mechanism of FIG. 22.

FIG. 26, depicts a cutter head according to the present invention.

FIG. 27, depicts a cross-section view of the cutter head of FIG. 26.

FIG. 28, depicts a top view of a blade according to the present invention.

FIG. 29, depicts a side view of the blade of FIG. 28.

FIG. 30, depicts a top view of a blade according to the present invention.

Figure 31:
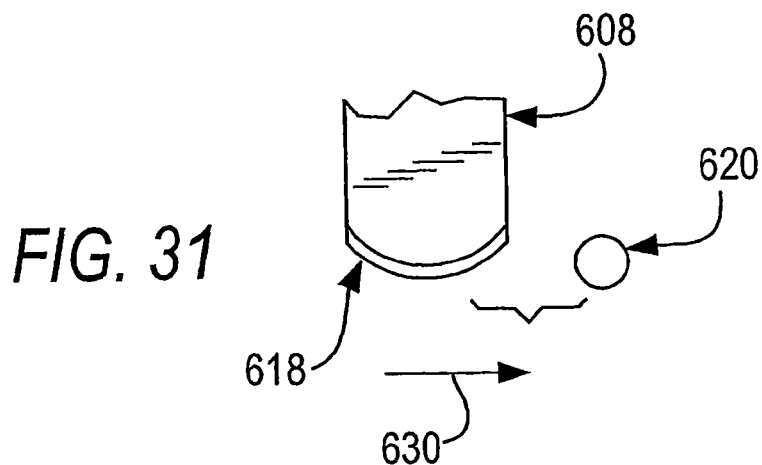
Figure 32:
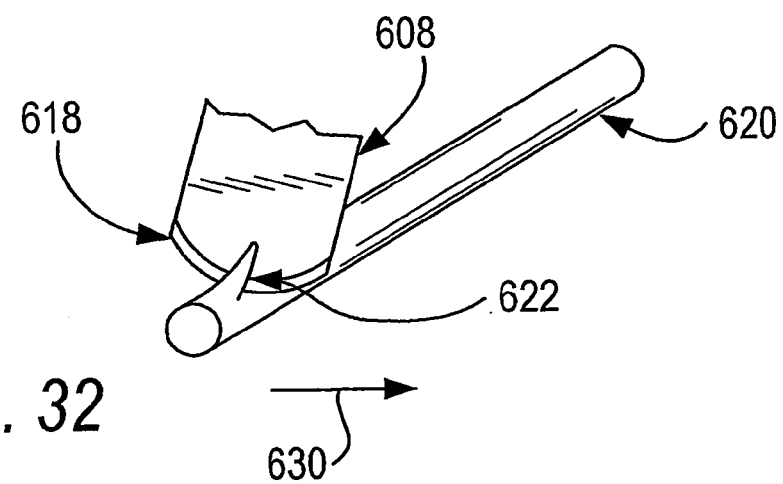
Figure 33:
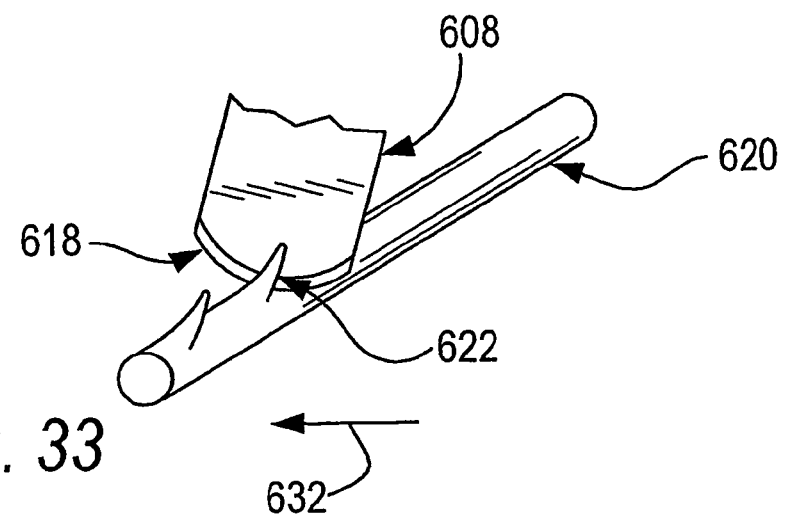

FIGS. 31-33 depict a two direction cutting motion using the blade of FIG. 30.

Figure 34:
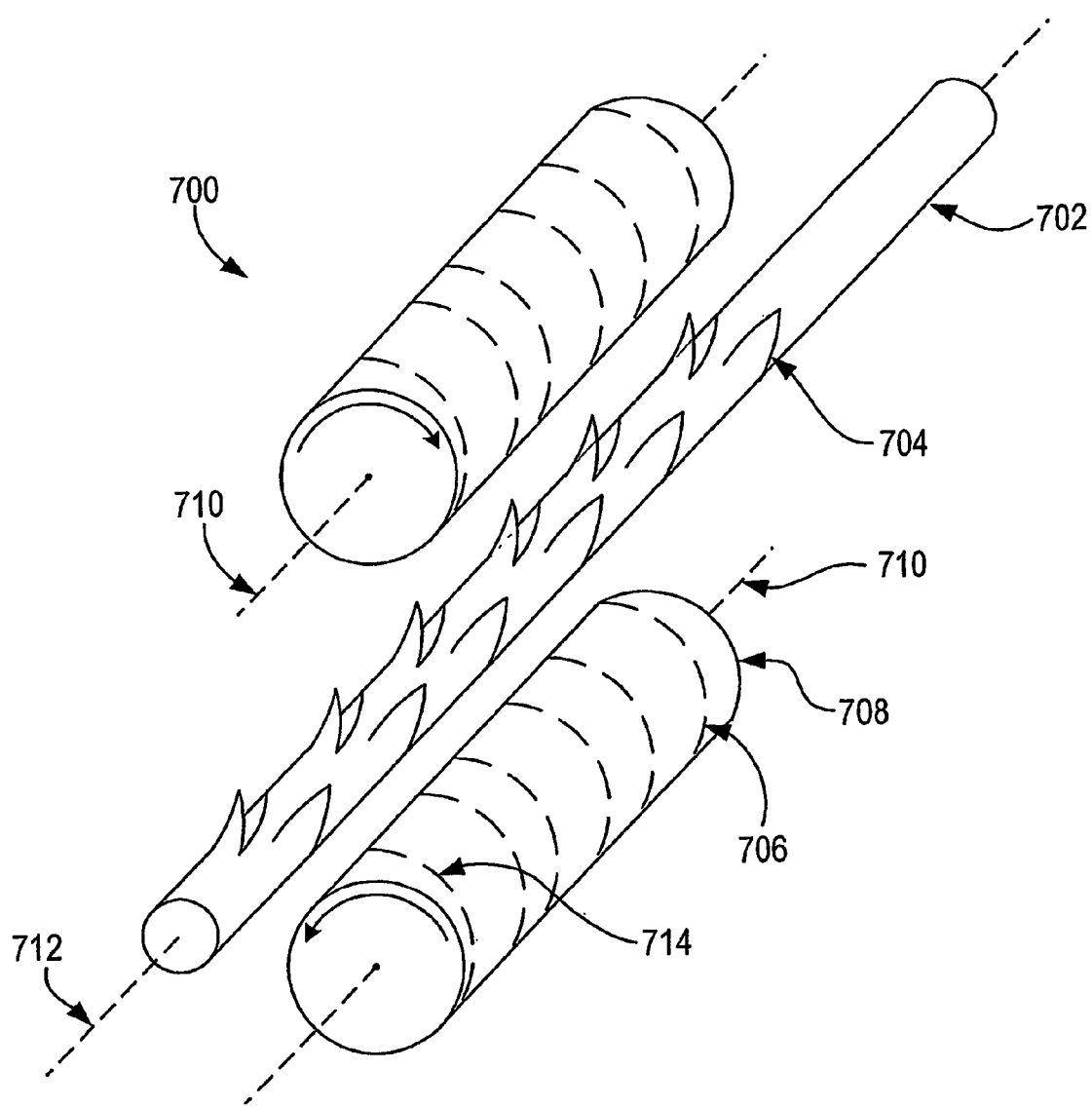

FIG. 34, depicts a planetary cutting mechanism according to the present invention.

DETAILED DESCRIPTION OF THE PREFERRED EMBODIMENTS

The present invention relates to an apparatus for forming barbs on a suture filament. Various components of the apparatus are also described each of which represents a novel aspect of the present invention.

Figure 1:
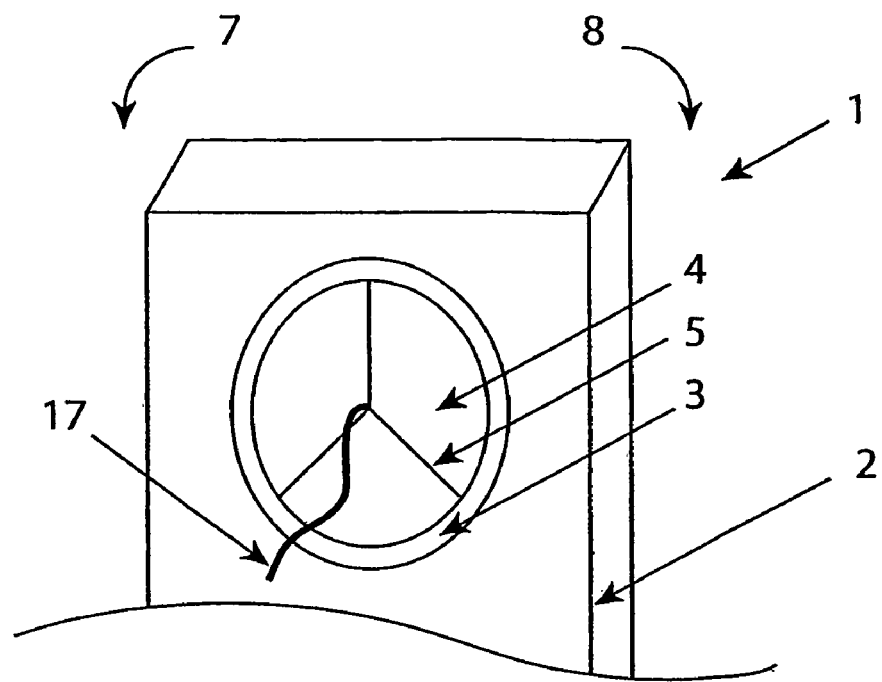
FIG. 1, depicts a perspective view of a collet with a three jaws.
Figure 5:
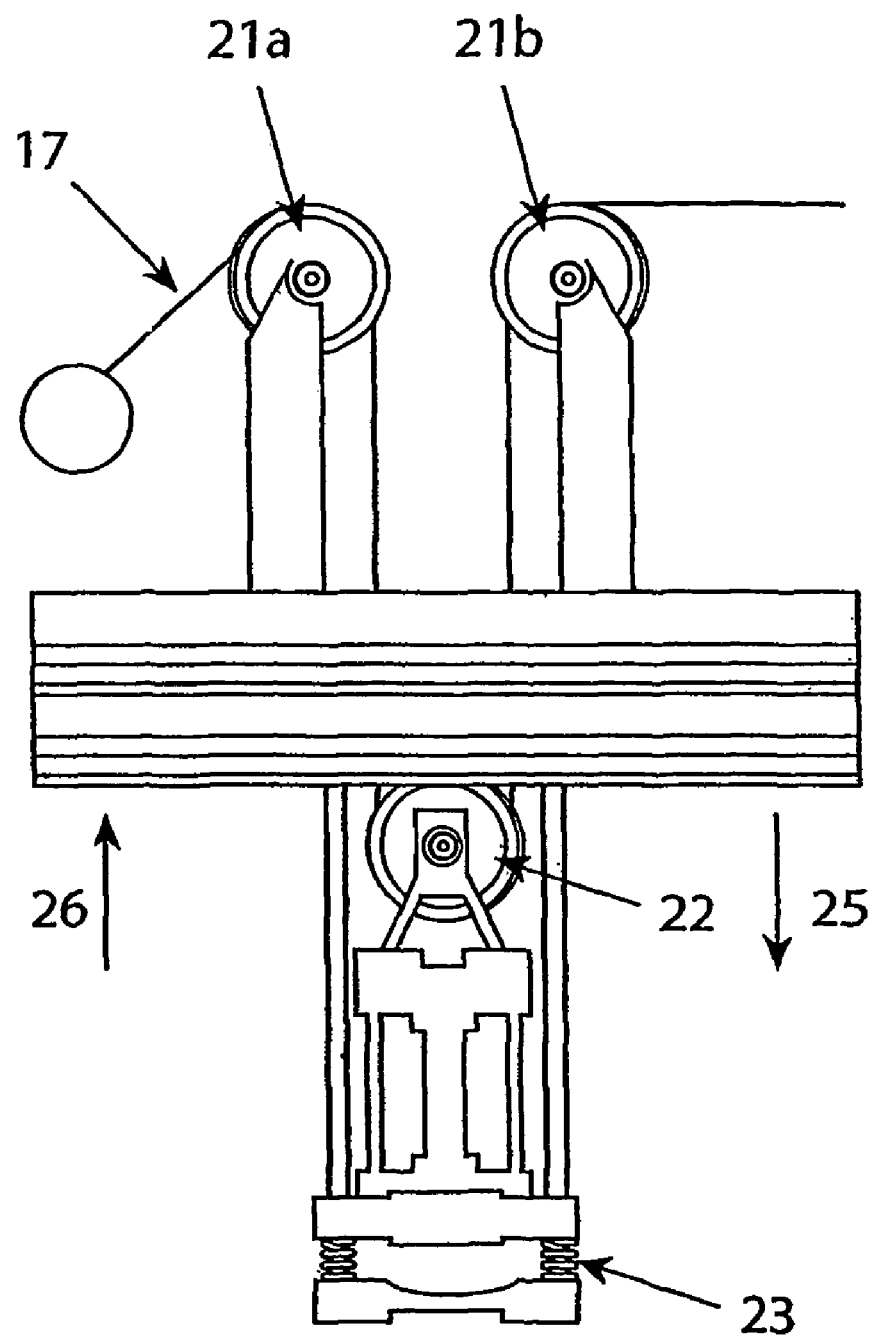
FIG. 5, depicts a perspective view of a filament tensioner.
Figure 10:
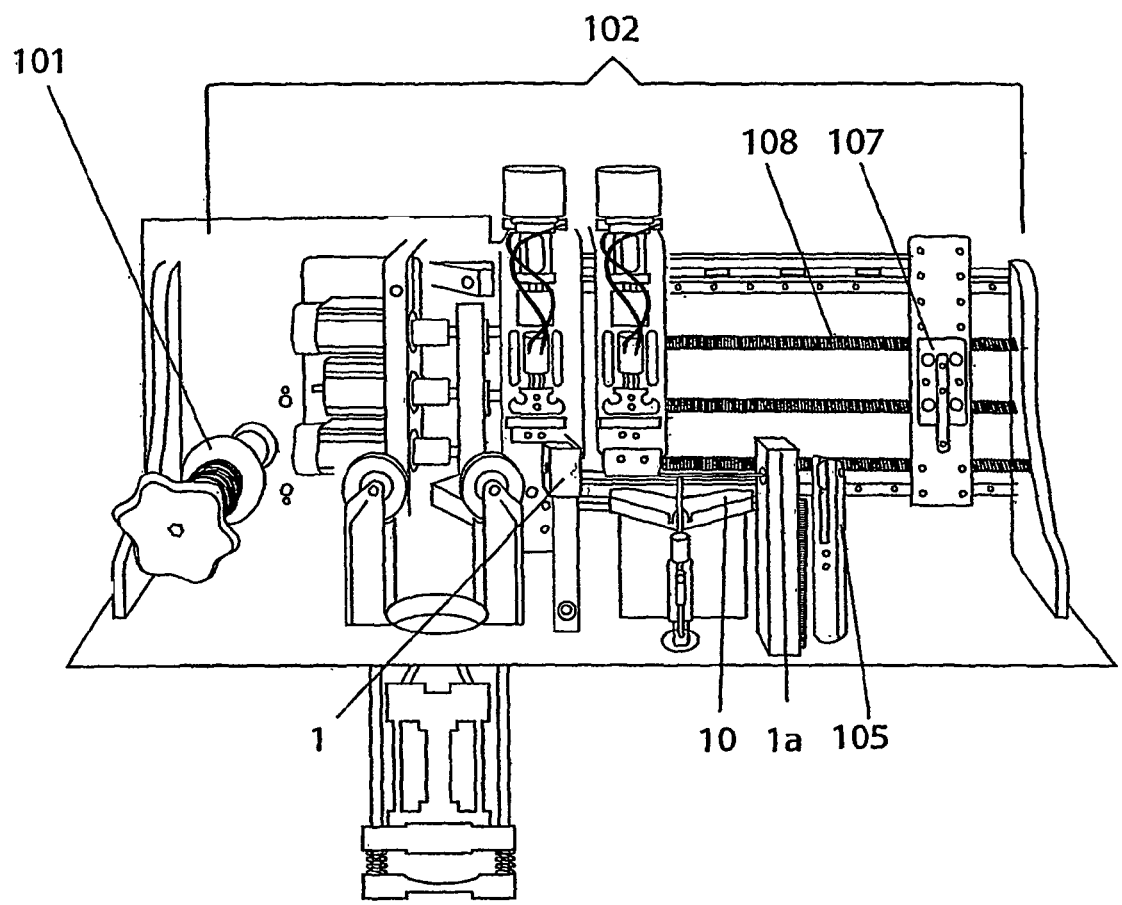
FIG. 10, depicts a perspective view of the apparatus.

The apparatus as shown in FIG. 10 comprises a filament supply 101. The filament supply is preferably spool as shown in FIG. 10. The filament supply 101 may optionally be motor operated. A filament 17 from the filament supply 101 is threaded through a tensioner 20, as show in FIG. 5. From the tensioner 20, the filament is threaded to an in-feed collet 1. The filament is then threaded through an out-feed collet 1a, and tensioned by the tensioner 20. The tensioned filament is held between the closed in-feed and out-feed collets 1, 1a. Between the in-feed and out-feed collets 1 and 1a, the filament is placed upon a holder or cutting bed 10, which supports the filament during the cutting process. The filament is held firmly by chuck, 3, of the in-feed and out-feed collets when closed as shown in FIG. 1. The cutting assembly 102 is then arranged to cut the barbs.

The cutting assembly 102 comprises a plurality of directional feed motors 103 that operate drive screws 108 for moving the cutters 106 longitudinally along the filament. Preferably the directional feed motors 103 are stepper motors which can accurately control the location of the cutting heads 106, shown in FIG. 11. The cutting assembly 102 also comprises a cutting motor 109 for articulating the cutters 106 and a height adjusting motor 110. The various motors permit the independent motion of the cutters along the vertical, longitudinal, and perpendicular directions relative to the filament. The motors may further move in varying degrees of motion relative to the other motors to enable the barbs to be cut in various lengths, depths, and shapes.

Figure 11:
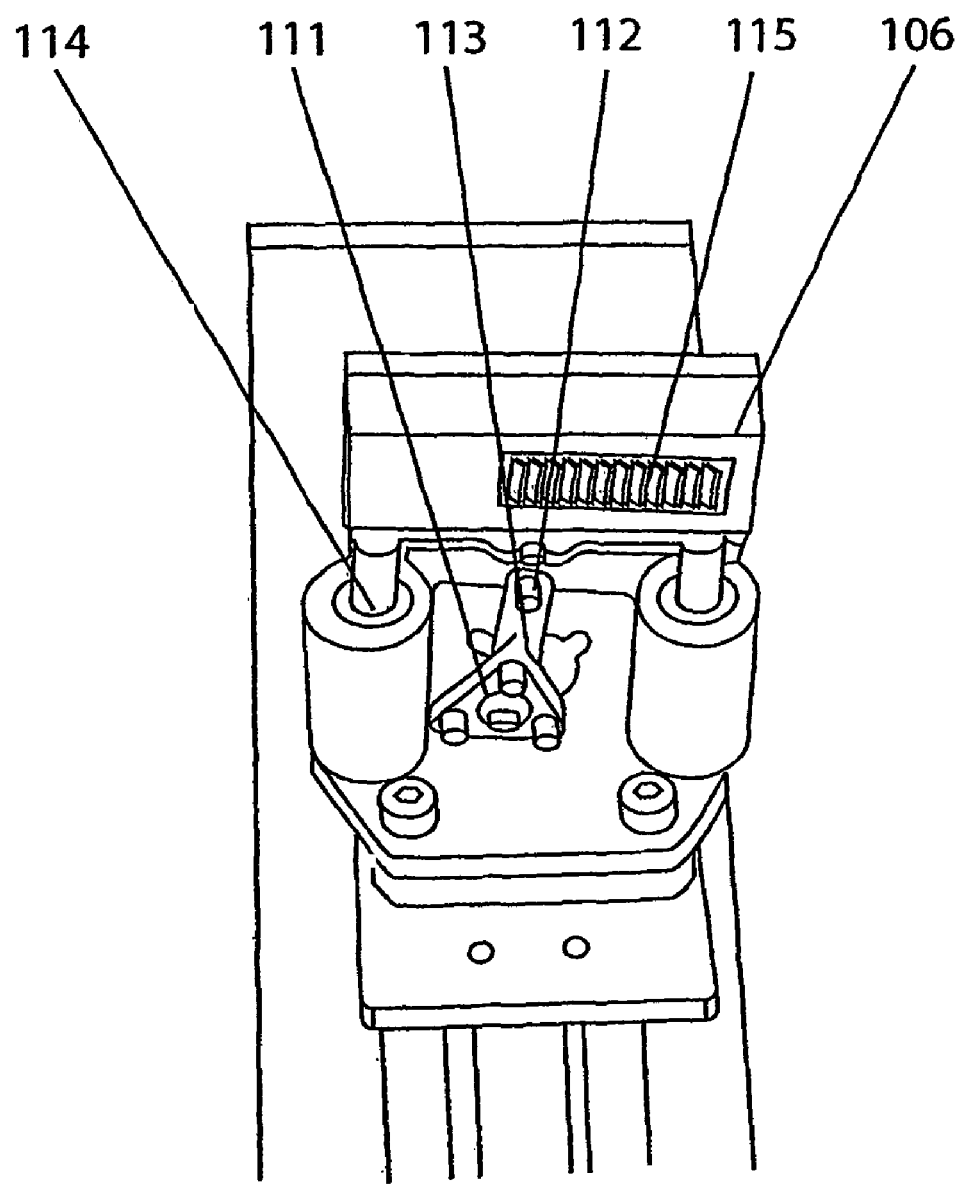
FIG. 11, depicts an underside perspective view of the cutter.

In the preferred embodiment the cutters 106 are oscillated to effect a cutting motion. This may be performed as shown in FIG. 11, through the use of an offset coupling 111 connected to the shaft of the cutting motor 109 and a pin 112 attached to the cutters 106. As the cutting motor 109 turns, the offset coupling 111 forces a link 113 to impart a force on the cutters 106. This force propels the cutters in a direction substantially perpendicular to the longitudinal direction of the filament. To ensure that only linear motion is imparted on the cutter 106, sliding rams 114 are used. Sliding rams 114, when used in conjunction with the pin 112, and the offset coupling 111 assist in transferring any rotational motion imparted on the cutter by the cutter motor 109 to linear motion and prevent any rotational force to be applied to the cutters 106. In effect the cutters 106 saw into the filament.

The height adjusting motor 110 insures that the cutters 106 are properly positioned over the filaments for cutting. The height adjusting motor 110 also lowers the cutters 106 during the cutting of the barbs to create a barb of a desired depth into the filament. Again, due to the precise nature of the movements, a stepper motor is used in the preferred embodiment.

In operation, a first cutter 106 is operated by a first directional feed motor 103 that moves the first cutter 106 in a first direction along the longitudinal axis of the filament. A second directional feed motor 103 moves a second cutter 106 in an opposite direction along the longitudinal axis of the filament. And a third directional feed motor 103 controls the movement of the grasping tool 107.

During the cutting of barbs, the directional feed motors 103 may move the cutters 106 linearly along the filament to force the barb away from the filament which gives the barb better holding power when in use.

Figure 12:
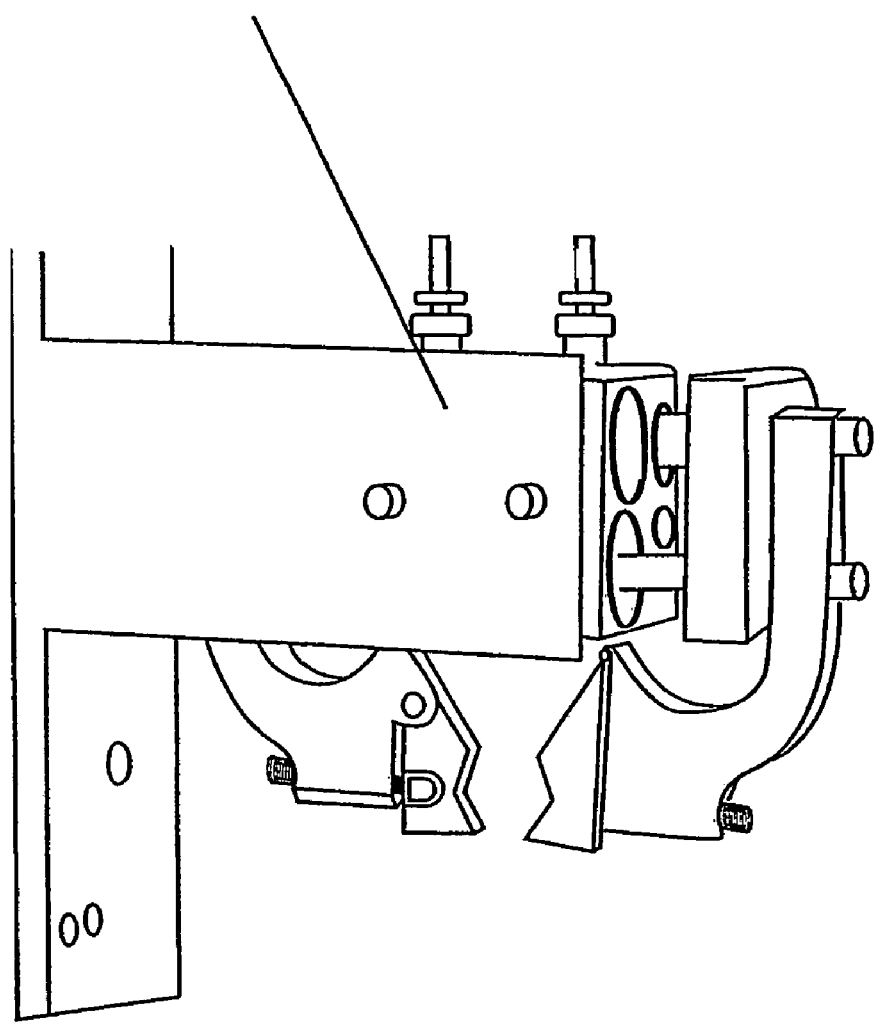
FIG. 12, depicts a close-up perspective view of the grasping tool.
Figure 13:
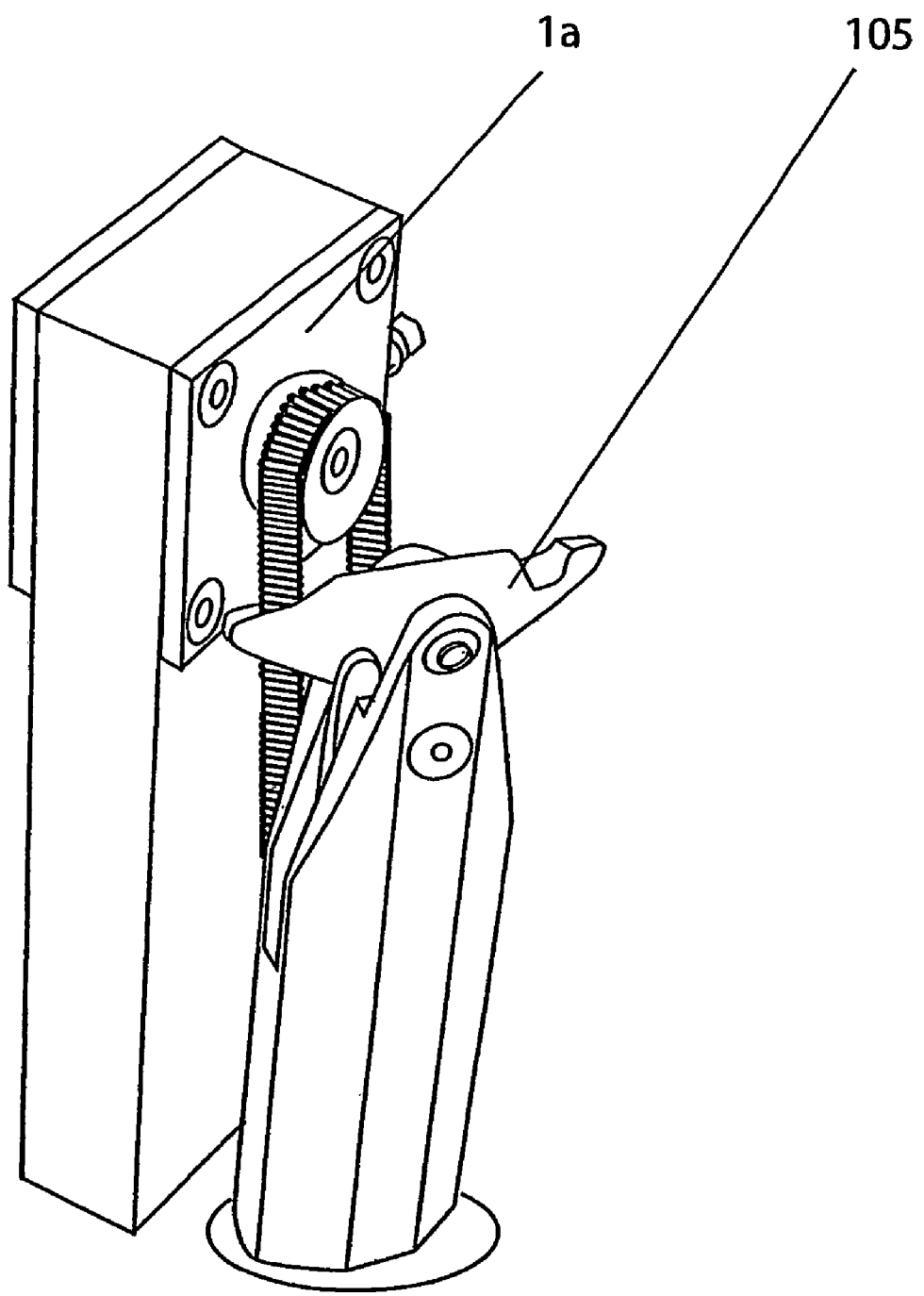

After the barbs are cut onto the filament, the filament is advanced, so that the next suture may have barbs cut therein. The advancement method may comprise a simple motor operated drum and spool (not shown) as the filament supply, or preferably a grasping tool 107 operated by a directional feed motor 103, and driven by a drive screw 108 as seen in FIGS. 12 and 14. The grasping tool 107 grasps an end of the filament that protrudes from the out-feed collet 1a. The grasping tool 107 is then advanced away from the out-feed collet 1a by the directional feed motor 103. Upon reaching a specified distance the out-feed collet 1a closes and a severing blade 105 cuts the filament to produce the suture.

The opening and closing of the grasping tool may be performed in a variety of ways including, but not limited to electromagnetic relays, pneumatic actuation, and hydraulic actuation.

The sutures, once cut, may be packaged for later application of needles or hooks or a hook attachment device (not shown) may immediately place hooks on the suture before packaging. In the latter scenario, a hook is attached to the end of the filament that protrudes from the out feed collet 1a while the barbs are being cut into the filament. After the barbs are cut, the grasping tool 107 draws the filament out to be cut to length and the second hook is applied after cutting. The grasping tool 107 then releases the completed suture for later packaging.

It is preferable that the cutting of the barbs occurs in two opposite directions on the filament, as the barbs are intended to allow movement of the suture in only one direction. Having two opposing sections of barbs, the surgeon or medical personnel placing the suture can insure that the suture will not come undone once placed. Accordingly, the present invention allows for cutting of barbs in two opposing longitudinal directions of the filament, without the need to reverse the filament or the cutting blades.

Typically, the cutting assembly 102 has two cutters 106, one for cutting barbs facing a first direction and one for cutting barbs facing a second direction. In instances where a long section of barbs is desired, the cutters 106 may be moved by the directional feed motors 103 after cutting the first set of barbs to initiate a second or more sets of barbs to create a seamless transition from section to section of the barbs. In such instances it may become necessary to cut two or more sections of barbs in a first direction, advance the filament, and then cut two or more sections of barbs in the second direction.

The cutter 106 may be formed of a plurality of cutting blades 115 as shown in FIG. 11. While in the preferred embodiment they resemble those described with respect to FIG. 6 other cutting blades may also be used.

The cutters 106 and their operational motors 109 and 110 ride on bearing tracks 118 which limit the friction that must be overcome by the directional feed motor 103 to move the cutter 106. In a preferred embodiment, the cutter is mounted on two bearing tracks 118 connected by a plate 116. A follower 117 is mounted on the plate 116, the drive screw 108 is threaded through the follower 117. The follower 117 has internal threads matching those of the drive screw 108. The directional feed motor 103 in turn drives the drive screw 108, which in turn acts upon the follower 117 and the attached plate 116 to position the cutter 106. The directional feeds 103 are preferably stepper motors although other motors may be used. The stepper motor allows for finite control of the directional feed necessary to achieve the desired finish to the suture. By use of the stepper motor the exact position of the cutters 106 relative to the filament 17 can be accurately and repeatably ascertained. The cutters 106 can be manipulated by the barb cutting apparatus to enable a wide variety of shapes of barbs to be cut into the filament 17.

Figure 3:
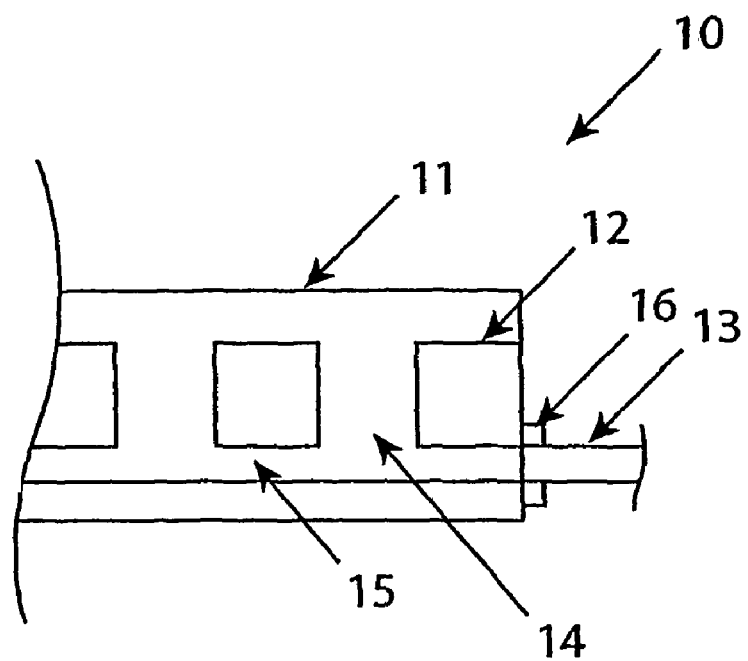
FIG. 3, depicts a profile view of a filament holder.
Figure 4:
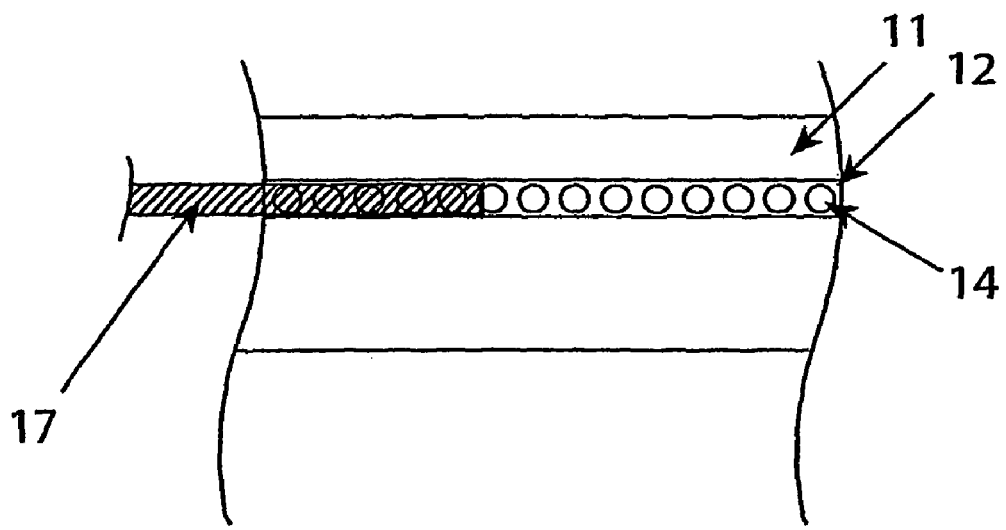
FIG. 4, depicts a top view of a filament holder.

In FIGS. 3 and 4, a holder 10 for securing a filament in accordance with another aspect of the invention is shown. The holder 10, secures the suture from lateral movement while barbs are cut into the filament. The holder provides a uniform profile for the cutting step and spreads the retention force along the length of the filament 17. The spreading of the retention force avoids acute stresses that can damage the filament 17 during the cutting process. The holder is preferably comprised of a bed 11, and the bed is preferably made of steel or other machinable metal. Alternatively, the bed could be made of plastic, glass, ceramic or any other material suitable for the purpose. The bed surface is preferably machined flat and operates as a working surface for the cutting assembly 102. The bed has a channel 12 machined into the exposed surface of the bed. The diameter of channel 12 is preferably the same as or slightly greater than the diameter of the suture material to be cut. The depth of channel 12 is preferably shallower that the diameter of the filament into which barbs are to be cut. Along the bottom of the channel 12 are a series of orifices 14. Each orifice is preferably connected in common to a bore 15. The bore 15 is connected to a vacuum or suction means 13 for drawing a vacuum on the bore 15 and the orifices 14. The vacuum means 13 for drawing a vacuum on the bore 15 and the orifices may simply be a tube or pipe connected to a vacuum source as shown in FIG. 3. Such a tube may require a fastener 16 for connection of the vacuum means to the holder.

In operation, filament 17 is drawn through channel 12 of bed 11 of the holder 10 substantially covering the orifices 14. Suction is then applied to the vacuum means 13. The vacuum produced by the suction translates to the orifices 14, which in turn holds the filament 17 rigidly in place. Once the filament is held rigidly in place a cutting operation can be commenced to cut barbs into the filament 17.

Figure 2:
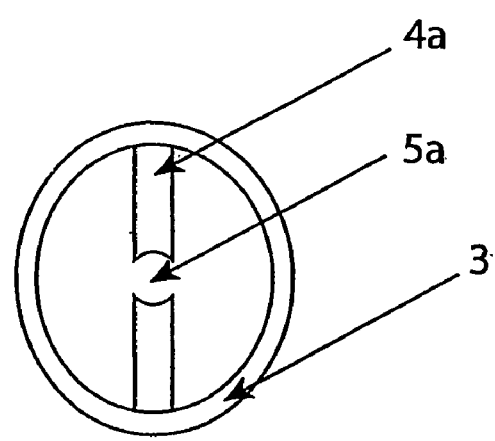
FIG. 2, depicts a front view of a chuck with two jaws.

A collet 1, in accordance with another aspect of the invention is shown in FIG. 1. The collet 1 holds a filament that has been threaded therethrough. The collet 1 secures the filament firmly without damaging the filament even during twisting. The collet 1 is comprised of a support 2 and a chuck 3. Chuck 3 has a plurality of articulating jaws 4, which may be opened and closed to facilitate the passing of a filament through the collet 1. The jaws 4 close to hold a filament. The jaws 4 are preferably finely machined so that they can close tightly around the filament without damaging it. The chuck 3 may house two jaws positioned, for example, 180° apart as shown in FIG. 2, or three jaws positioned approximately 120° apart as shown in FIG. 1, or more.

In the three jaw configuration as shown in FIG. 1 it is preferable that each jaw have a substantially flat gripping surface 5 which enables all three jaws 4 to simultaneously grip the filament 17. In the two-jaw configuration it is preferable that each jaw 4a have a concave gripping surface 5a. The concave gripping surface is sufficiently shallow to allow the jaws 4a to firmly hold the filament. The positioning and configuration insures that the jaws 4a apply even pressure to the filament and have good holding power without damaging the filament 17. Additionally, the jaws may be formed of a material that prevents contamination of the filament 17.

The jaws 4 and 4a are preferably pneumatically operated for closing the jaws and spring biased to open the jaws, in a normally open jaw configuration. Alternatively, a normally closed jaw configuration could be utilized where the pneumatic pressure opens the jaws and the spring force closes them. Additionally, one skilled in the art would appreciate that the jaws could be opened and closed by alternative means. For example the jaws could be opened and closed by electromechanical, hydraulic, or simple mechanical threading means as in a drill bit chuck.

The chuck 3 of the collet 1 is preferably rotatable. Rotation of the chuck 3 facilitates the imparting of twist to a filament held by the jaws 4 or 4a. By imparting twist, the cutting assembly 102 is able to cut in a single pass barbs on the filament that are offset from one another when the filament is untwisted. Offset barbs may also be achieved by cutting of the untwisted filament, and then rotating the collet to rotate the filament into a twist. Filaments are known to retain a twist conformation after twisting—a characteristic which may be enhanced by an annealing step. Annealing entails the application of heat to the suture strand and may be useful in the long term preservation of a specific suture conformation. Annealing may be of particular interest where it is desired to generate and maintain a helical array of barbs by deforming, e.g. by twisting a suture, either before or after cutting a series of barbs in an unconstrained suture filament. Annealing may further be necessary to ensure stable product geometry during long term storage and/or high temperature exposure.

If the suture is to be annealed after deformation, annealing should be performed as soon as possible after the suture has been placed in the desired conformation. Generally, the annealing temperature should be above the glass transition temperature but below the melting temperature of the polymer to achieve optimum results. Annealing may also be used as a pre-processing step for the suture material that adds a conformation that is useful later in the manufacture of a barbed suture.

Alternatively, or in conjunction with annealing, the application of a non-linear packaging method may further improve long term retention of suture geometries such as a twist. Several packaging methods are available that employ a non-linear product arrangement such as a raceway. By packaging a suture in a non-linear fashion, the ability of the suture's geometry to return to its natural state is resisted. This may be of particular interest where the method of obtaining a helical array of barbs leaves significant internal stresses within the product that may have a tendency to relax over time or when subjected to moderate or extreme storage conditions. For further discussion of the practice of twisting the filament before and after cutting barbs see U.S. patent application Ser. No. 09/943,733, the disclosure of which is incorporated herein by reference. The rotation of the collet is preferably actuated by an electrical motor. However pneumatic, or hydraulic means could also be employed without departing from the scope of the present invention.

Preferably the barb cutting apparatus comprises two collets an in-feed collet 1, and an out-feed collet 1a. Either one or both of these collets may be rotatable. However it is preferable that at least the out feed collet is rotatable. Further, it is preferable that the out-feed collet 1a be rotatable in both a first direction 7 and second direction 8. This facilitates both the imparting of twist on a filament and the removing of twist from the filament. However, there may exist applications, and filament fibers for which imparting and maintaining twist is preferable for storage or other applications. In such applications the filament can be twisted and untwisted as desired, either before or after cutting, without departing from the scope of the present invention.

The present invention further relates to a tensioner 20 for tensioning a filament 17. The tensioner 20 comprises pulleys 21 and 22. The pulleys consist of stationary pulleys 21a and 21b and movable pulley 22. The tensioner 20 ensures that the filament 17 is constantly under a relatively uniform tension throughout any of the advancement, twisting and barb cutting steps regardless of their sequence.

The filament is preferably run over a first stationary pulley 21a, under a movable pulley 22, and then over a second stationary pulley 21b. In a preferred embodiment, a springs 23 act as limiting devices stopping the movement of the moveable pulley 22 in a first direction 25. The movable pulley is weighted, this weight tensions the filament as it is drawn through the collets by the gripping tool 107. The movement of the filament by the gripping tool 107 causes the movable pulley 22 to move in a second direction 26. Accordingly, the length of travel of the movable pulley 22 is approximately equal to maximum length of a suture. Upon stopping movement in the second direction 26, the filament supply 101 slowly rotates to allow the filament to be pulled away from the filament supply 101 and in the direction of the stationary pulley 21a. This allows the movable pulley 22 to move in the first direction 25 until contacting the springs 22. The filament supply 101 is most preferable operated by a stepper motor which can gradually advance the filament until the movable pulley 22 contacts the springs 23. Sensors may be added to stop the motor when the movable pulley reaches a predetermined position.

In use, the tensioner 20 ensures that filament 17 which spans from an in-feed collet to an out-feed collet is properly tensioned. Tensioning is necessary to ensure that the filament 17 can be properly twisted either before or after having barbs cut therein. Tensioning of the filament 26 further assists in preventing the filament from moving during the cutting process and insures proper alignment of the filament 17. The initiation of the supply of the filament by the rotation of the filament supply 101 is not begun until after the in feed collet 1 has closed on the filament. This insures that there is always tension on the filament.

Figure 7:
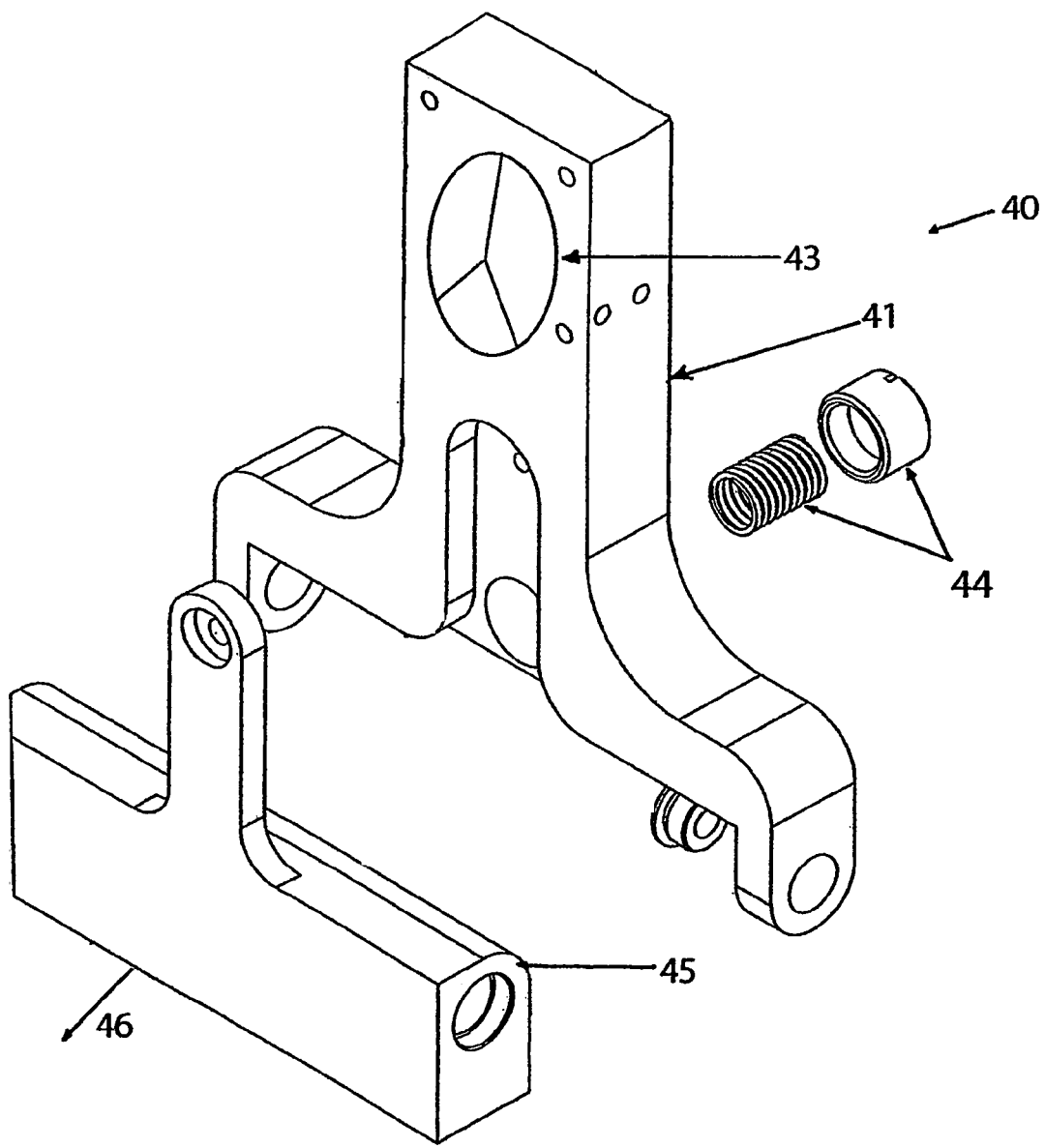
FIG. 7, depicts a collet equipped with a biased tensioner.

The present invention still further relates to a collet 40 having a collet tensioner 44. It is understood that when a filament is twisted, the length of that filament will be decreased. Accordingly, when the filament is firmly grasped at two ends the force required to twist the filament is transferred into a longitudinal tension force acting on the filament. If the force were of sufficient magnitude, the filament could break. To avoid this, at least one of the collets 40 of the cutting apparatus may be equipped with a collet tensioner 44. The collet tensioner 44 may be comprised of a simple spring as shown in FIG. 7. In the collet 40 shown in FIG. 7, the support 41 of the collet 40 is rotatable about a pin 46. The pin passes through the support 41 and the collet base 45. The collet tensioner 44 acts against the base 45 in the longitudinal direction of a filament threaded through the chuck 43 housed in the collet 40. The tension imparted on the filament by collet tensioner 44 may be adjusted by screw cap 5 which increases or decreases an initial spring tension imparted on the collet 40. This adjustment enables the apparatus to be useful for a wide variety of filament materials.

In operation, when the filament is twisted, the force of the shortening causes the collet 40 to be pulled in the longitudinal direction of the filament. The collet tensioner 44 allows for the collet 40 to move in that direction when sufficient force is imparted on the collet 40 to overcome the resisting spring force of the collet tensioner 44. The pin 46 provides an axis about which the collet 40 can rotate. This movement insures that the force imparted on the filament never exceeds the spring force of the collet tensioner 44. Accordingly, the spring force of the collet tensioner 44 can be regulated to insure that the filament is never tensioned to the point of breaking.

Figure 6:
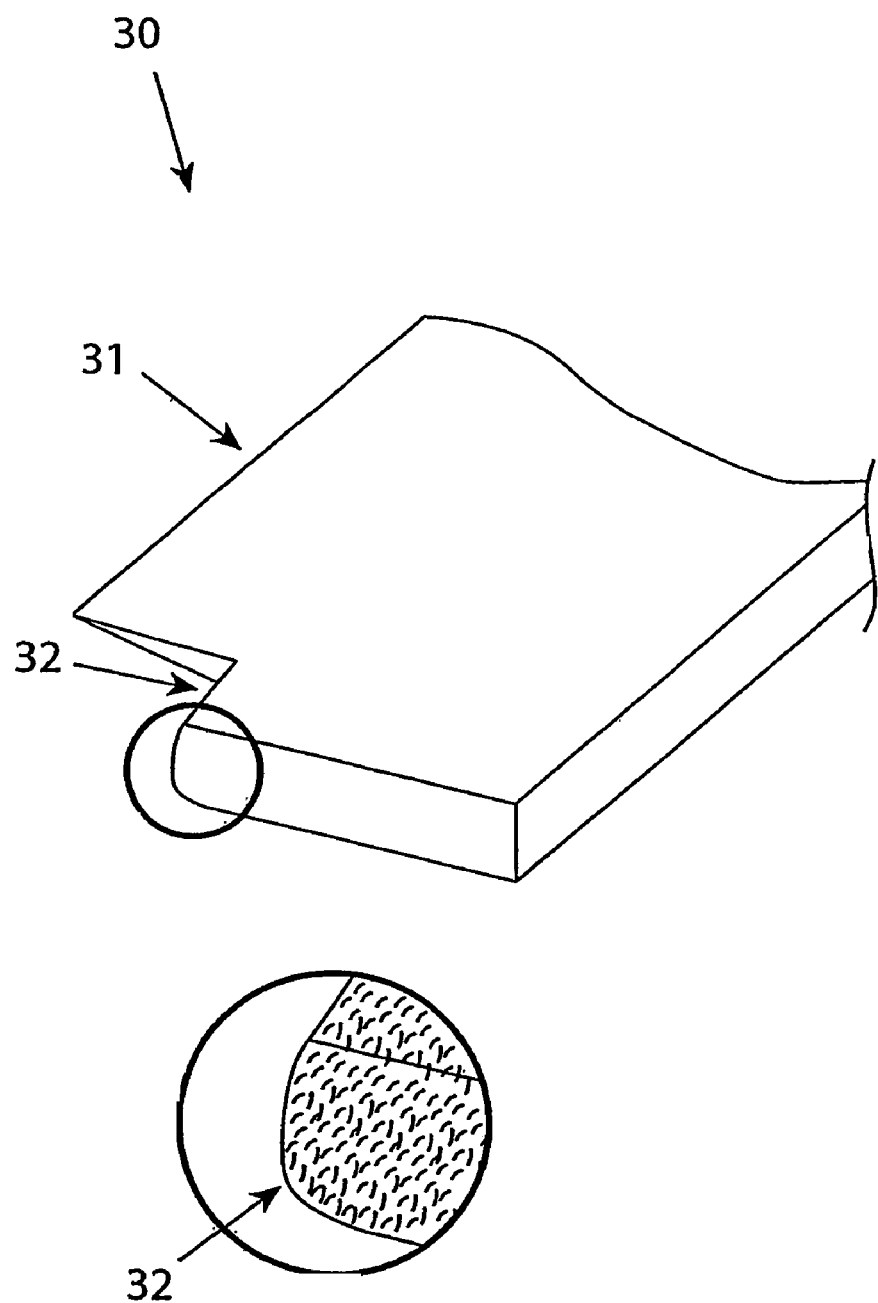
FIG. 6, depicts a perspective view of a cutting assembly with magnified view.

As shown in FIG. 6, another aspect of the present invention relates to a cutting blade 30 for cutting barbs into a filament. FIG. 6 shows a cutting blade having a sharply honed edge 31. This is the primary cutting edge of the cutting assembly and is used for the initial cutting of a barb in a filament. Following the first edge is a second edge 32. The second edge is preferably blunted, textured or rounded, as shown in the magnified view of the cutting assembly 30, FIG. 6. The textured and blunted features of cutting blade 30 act to roughen the interior surfaces of the barb section of the filament. This is preferable because it has been observed that a roughened texture on the interior surface of a barb imparts greater holding ability. This gripping ability insures that the suture is less likely to slip when threaded through tissues by a surgeon or other medical personnel. Alternatively, cutting blades with ends that are arcuate can create an arcuate shape at the base of the barb so as to reduce the sheering stress focused at the vertex of the barb.

In operation, the cutting blade is typically drawn across and into the filament to be cut As such, the sharply honed first edge 31 cuts the barb in the filament to the desired depth and at the desired angle to the filament. The second edge 32 is subsequently drawn along the previously cut barb and roughens the interior surfaces of the barb.

In yet another aspect of the present invention the cutting blade is held by a robotic arm and performs the cutting of the filament in an articulated, motor controlled action. The robotic arm holds a plurality of cutting blades and locates the cutting blades over the filament. In one aspect of the robotic arm embodiment, the cutting blades oscillate in a cutting motion while being lowered onto the filament by the robotic arm. Further, the robotic arm may angle the cutting blades to form the barbs on the filament.

Figure 8:
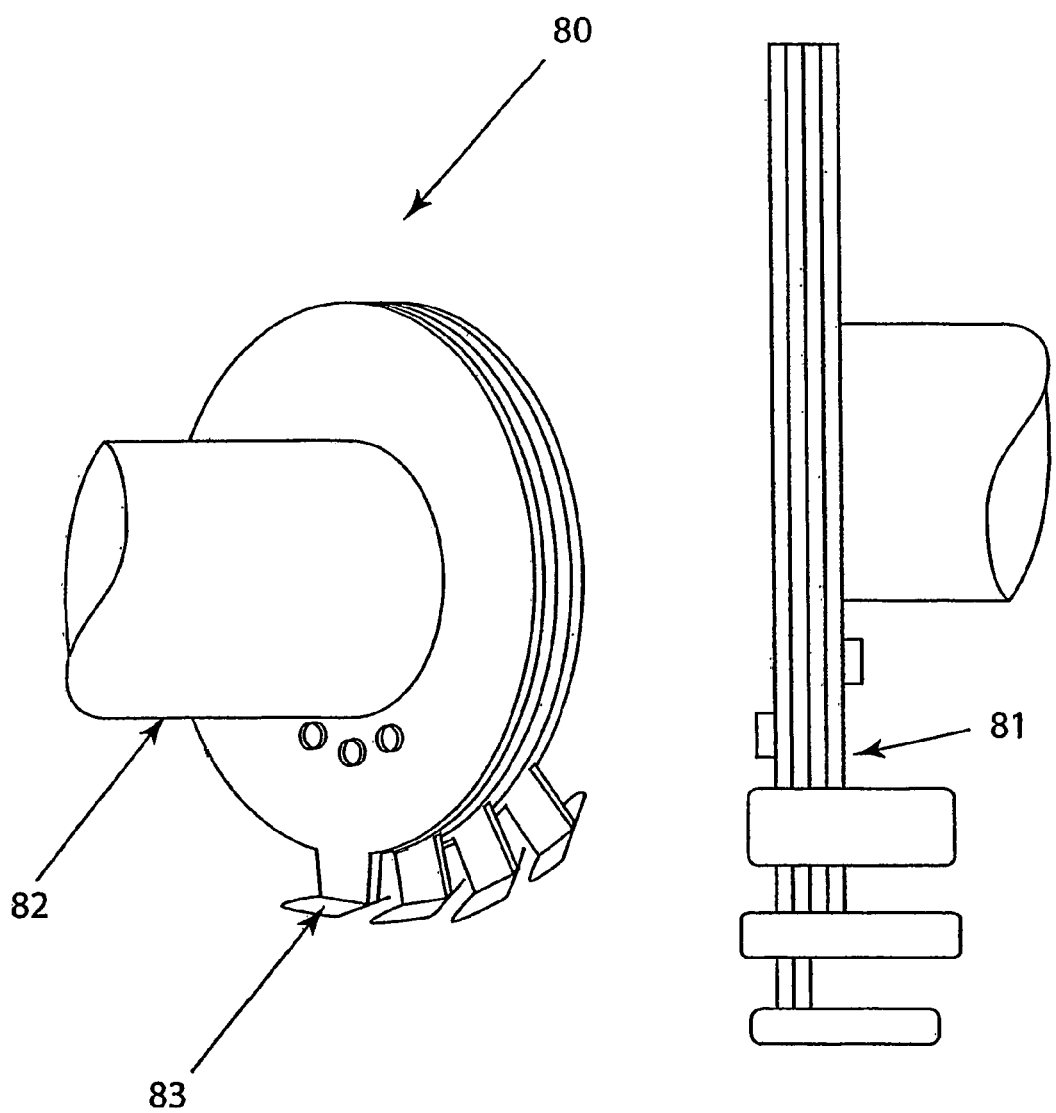
FIG. 8, depicts a rotational barb cutter mounted on a shaft.
Figure 9:
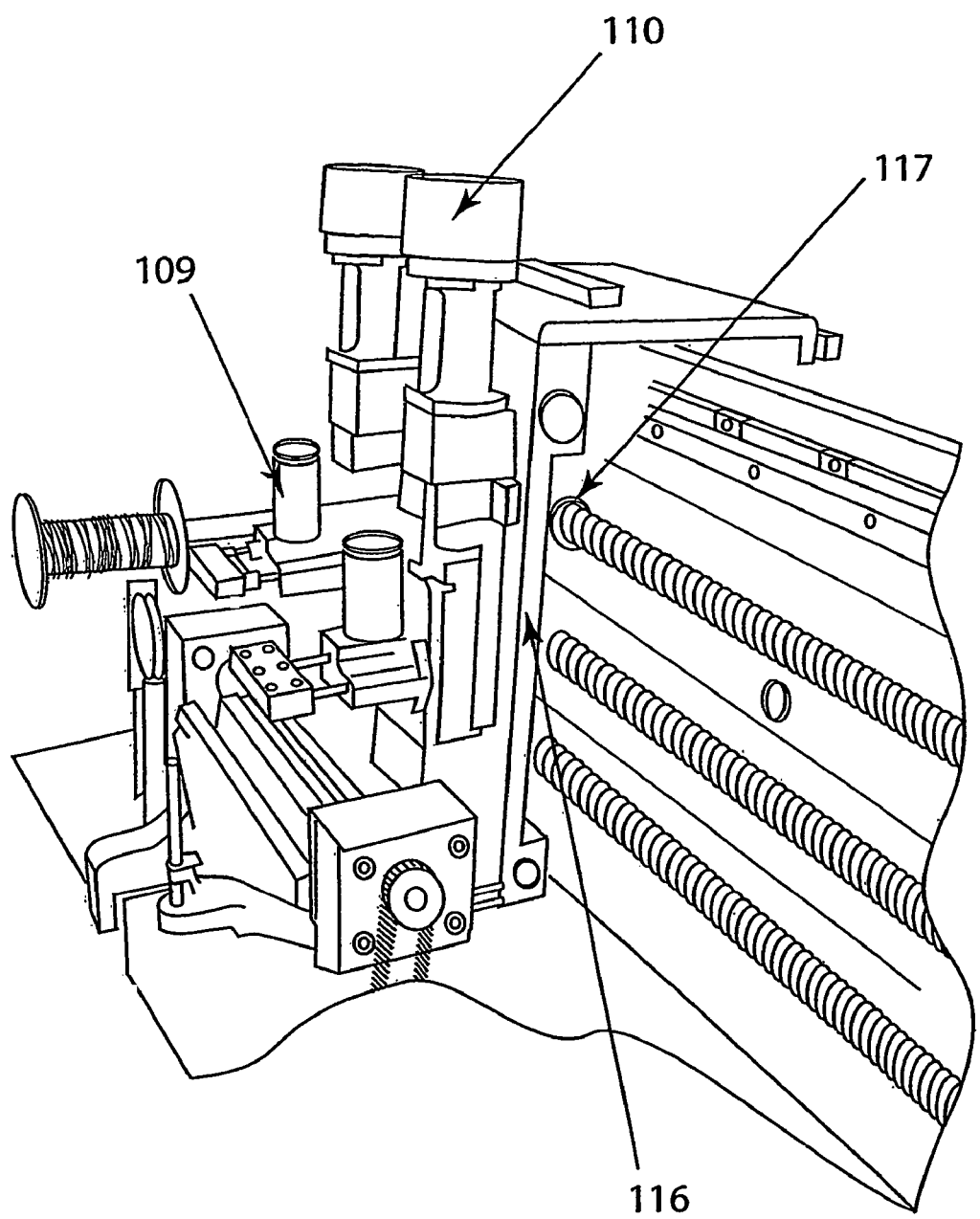
FIG. 9, a perspective view of the cutting assembly and the in-feed and out-feed collets.

Another aspect of the present invention relates to a cutter 80 that is comprised of a series of cutting disks 81 connected to a shaft 82, as shown in FIG. 8. The cutting disks have an angled tab extending from them. The tab is the cutting surface of the disk. The tab is angled at least 90 degrees from the disk. This angling allows for the barb to be displaced vertically from the filament which increases its gripping power when used. A plurality of disks are attached to a single shaft separated by spacers (not shown). On a single shaft disks with tabs facing in opposite directions can be attached to enable the cutting of barbs in both directions in a single operation. Alternatively, two cutters could be used, one for cutting the barbs in each direction. The tabs of the cutting disks are offset relative to one another such that the cutter can be positioned over a filament in which barbs are to be cut without initially contacting the filament. It is preferable that the cutter 80 makes one rotation to cut all of the barbs for a single suture, however, it may be necessary in certain applications to make more rotations particularly where a large section of suture is to be given barbs of a particular orientation. Finally, the tabs 83 may be given a variety of cutting shapes and attributes, these include but are not limited to cup shaped blades, tear dropped shaped blades, and roughed blades, as shown in FIG. 6.

Another embodiment of the present invention is the cutting mechanism 200 shown in FIG. 16, which comprises a vise bed 202 having no moving parts. In FIG. 16 the suture 204 is held in semicircular groove, not shown, formed on one side of the vise bed 202 to prevent the suture 204 from moving laterally during the cutting operation. The suture 204 is tensioned by moving the vise bed 202 vertically while the suture is held in place and prevented from slipping by the first and second collets 206a and 206b. The vise bed 202 may substantially conform to the shape of the arc created by the tensioning of the suture 204.

In a further embodiment of the present invention, the vise bed 202 and cutting heads 208 are mounted to a moveable plate 210. This reduces the number of individual tolerances and thereby the tolerance stack up between the vise bed 202 and blades 212.

The movable plate 210 is movable in at least two directions, for example vertical and horizontal. Movement in the vertical direction tensions the suture 204 while movement in the horizontal directions allows for cutting to occur across the span of the suture 204, between the first and second collets 206a and b. Movement of the cutting head 208 relative to plate 210 in a direction perpendicular to the horizontal direction moves the blades 212 across the suture 204 and allows the blades to form the barbs.

In one example, to avoid damaging the suture 204, the vise bed 202 may begin at the outfeed side near the second collet 206b and move towards the infeed side near the first collet 206a. In the example shown in FIG. 16 two cutting heads 208 are used, each with a single fixed blade 212, that is moved in the direction perpendicular to the longitudinal axis of the suture 204 to cut the barbs.

The blades 212 can undertake a variety of motions in forming the barbs on the suture 204. One example of the blade motion is substantially square. In the square or rectangular motion the blade 212 traverses perpendicular to the longitudinal axis of the suture 204 to cut a barb. The blade 212 is then moved in the horizontal direction along the longitudinal axis of the suture to a predetermined and customizable point. The blade 212 then is drawn back across the suture but at a height that prevents the blade 212 from engaging the suture 204 and the formation of a barb. One skilled in the art will recognize that a variety of methods could be employed to ensure the blade 212 cuts while moving in one direction but does not cut when moving in a substantially opposite direction. For example a cam or ramp system could be employed to ensure that the height of the blade 212 is altered when changing directions in its movement perpendicular to the longitudinal axis of the suture 204. Other examples include motor controlled indexing screws that alter the height of the movable plate 210 depending upon the direction of travel of the blades. In addition, the blade may also be designed to accommodate two-direction cutting. In such an example when performing the second motion perpendicular to the longitudinal direction of the suture 204, the blade 212 is not raised above the suture. An example of a blade that can be used for two-direction cutting is shown in FIG. 30, which will be discussed in detail below.

The above-described cutting mechanism 200 has several advantages including a decrease in the tolerance stack up for the various parts as they are mounted on a single movable plate 210. Further, the use of tension to hold the suture 204 in place may prevent damage to sutures made of certain suture materials that may occur when barbs are cut using a vise, as discussed above, that uses compressive forces to secure the suture. And as there is a reduction of moving parts the accuracy of the cutting mechanism 200 is improved.

Another advantageous embodiment of the present invention is shown in FIGS. 17 and 18 and includes a blade 312 mounted on a 4 bar mechanism 310. The 4-bar mechanism is connected to a series of gears that provide a rotating motion of the cutter head 308 to form barbs on the suture 304. The motion of a lead screw 314 causes a follower gear 316 to propel the four-bar cutting system 300 along the longitudinal axis of the suture. The cutting head's 4-bar linkage 310 is connected to the lead screw 314 and the follower gear 316 by a spline gear system 318. The spline gear system imparts rotational force to the 4-bar linkage 310 that allows multiple cuts to be made in succession while the cutting head 308 is moved down the length of the suture 304.

The cutting head 308 is moved in a substantially circular motion describing an arc 306 by the spline gear system 318 and connected 4-bar linkage. One direction of movement of the blade 312 is substantially perpendicular to the longitudinal axis of the suture 304 for cutting barbs in succession, while the rotational movement of the blade 312 is at a desired angle to the suture 304. The blade 312 is angled approximately at the same angle at which the barb is to be formed as shown in FIG. 18. Because the motion of blade is permanently linked with motion of the four bar linkage and the lead screw the cutting head the four-bar cutting system 300 has the ability to cut barbs at high speeds.

In FIGS. 19, 20, and 21 yet another embodiment of the present invention is shown. In FIG. 19, a 3-axis robot 400 using a Cartesian coordinate arrangement directly controls the motion of the cutting head 402 in a "fixed" fashion (i.e., with minimal vibratory motion).

The robot 400 includes arm 404 for moving the cutting head 402 in the x-direction, arm 406 for moving the cutting head 402 in the y-direction, and arm 408 for moving the cutting head in the z direction. Blades 410 are maintained in the cutting head 402 with spacers 412 that maintain a consistent distance between the top of the vise 414 and the ends of the blades 410.

In one example shown in FIG. 20 blades 410 cut barbs in a single pass over suture 416. First the blades 410 are lowered to a point at which they can contact the suture 416, as shown in movement 420. Then the cutting head 402 is moved slightly in the x-direction while the cutting head 402 is brought across the suture 416 moving substantially in the y-direction, as shown in movement 422 of FIG. 20. The cutting head is then brought back over the suture in movement 424 in preparation for the next cut as shown in FIG. 20. Once all cuts have been made for barbs in one direction, the rotational activator 418 spins the cutting head 402 180° in movement 426 to produce barbs in the opposing direction as shown in movements 428.

By utilizing a spring 420 between the z-axis arm 408 and the cutting head 402, tolerances for the z-axis arm can be decreased because blade positioning is maintained by the spacers 412 on the bottom of the cutting head 402 that contact the top of the vise 414. Alternately, the spring and cutting head spacers could be removed to allow the z-axis arm alone to control depth of cut.

A further embodiment of the present invention is a corkscrew rotating cutting mechanism as shown in FIG. 22. The cutting mechanism 500 is formed of a single piece and can be rotated in a cutting direction 506. The cutting edges 502 are formed in a spiral around a central rod or shaft 504. The cutting mechanism 500 may be designed so that in use it has only a short period of time that it is in contact with a suture. For example, while being constantly rotated the cutting mechanism 500 may be raised and lowered on to a suture material to form barbs during just a small portion of its rotation. When the cutting mechanism 500 is lifted, the suture material may be advanced to allow the cutting mechanism to cut barbs in a new location on the suture material or a new suture. The cutting mechanism 500 may also be synchronized with a suture that is continuously moving to produce a continuous feed of barbed suture material.

FIGS. 23-25 show a progression of three cuts being performed on a single suture that is being rotated to form a series of off-set barbs 512. By controlling the speed of the cutting mechanism 500 and raising and lowering the suture 510 onto the blades 502, the blades 502 cut a series of barbs 512. If the suture material 510 is rotated as shown in the progression from FIG. 23 to FIG. 25, the barbs are formed around the longitudinal axis of the suture 510. The movement of the suture can be optimized to increase or decrease space between the barbs both circumferentially and longitudinally. Other elements that can lead to optimization of the barb profile include the rotation speed of the cutting mechanism 500, the speed of longitudinal movement of the suture, and the speed of suture rotation. The timing of all of these can be varied to produce a desired barb profile and to avoid impinging previously cut barbs. This method produces barbs 512 which spiral about the central axis of the suture 510 without the need to twist the suture material as discussed above.

A further embodiment of the present invention is a drop-in blade cutter head assembly 600 as shown in FIGS. 26 and 27. The cuter head assembly 600 includes a cover 602. The cover 602 may include a compressible material 604 that applies a compression force to the back of the blades 608 which are inserted into a series of blade slots 606 and formed in the base 610. The compressive material 604 may run the entire length of the cover 602.

In one embodiment the blade slots 606 are cut at an angle Ø to an exterior surface 612 of the base 610. As shown in FIGS. 28 and 29, the blades 608 may include a machined angled flat 614. The angle of the angled flat 614 has an angle α formed at a desired angle to the longitudinal axis of the blade 608 and which corresponds to the angle Ø at which the slots 606 are formed in the base 610. The angled flat 614 works in concert with the slots 606 and the compressible material in the cover 602 to ensure that the blades 608 are maintained at a desired angle to the base 610.

In practice, blades 608 are inserted into each or substantially all of the slots 606. The cover is secured over the blades to hold the blades 608 in place. The cutter head may then be used in conjunction with a variety of barb cutting machines as described herein, including the 3-axis robot, and the apparatus shown in FIG. 10.

The drop in blades 608 may be sectioned from blade stock as shown in FIGS. 28-30. Blades 608 can be sectioned from blade stock so that the blade bevel is up or down. Blade bevel up means that the facet 616, which forms the cutting surface of the blade 608 faces away from the suture while cutting. Blade bevel down means that the facet 616 faces the suture when cutting.

Alternatively, the blades may be sectioned from circular blade stock as shown in FIG. 30. The resulting blade has a small radius to the cutting edge 618. One advantage of the blade 608 with radius cutting edge 618 is that it allows the cutting cycle to be initiated from either side of the suture.

The radius cutting edge 618 also allows for both a forward and a backward cutting pass as shown in FIGS. 31-33. In FIG. 31, the blade is positioned to the side of the suture 620, and has a motion in direction 630. FIG. 32 shows the barb being formed during a forward cut while the blade 608 is moving in the forward direction 630. FIG. 33 shows a second barb 622 being formed on the suture 620 during a backward cut or while the blade 608 is moving in the backward direction 632.

Another aspect of the present invention is a fluid jet cutting system that uses high-pressure liquid to form one or more barbs in the suture material. Using water jet cutting technology, a fine spray of high-pressure fluid can be used in combination with, for example the 3-axis robot discussed above, to controllably cut barbs into suture material in a fashion similar to the use of the blades 608. The cross section shape of the fluid jet and its movement are used to control the formation and shape of the barbs. For materials that are likely to absorb water alternative fluids are considered within the scope of the present invention. Further, timing of the cuts can be used to optimize the depth of the barb and prevent cutting through the material.

Yet another embodiment of the present invention is a planetary cylindrical cutter system as shown in FIG. 34. The planetary cutter 700 comprises two or more cylinders 708 with a cutting blade/edge 706 spirally oriented about the cylinder 708. The cylinders rotate about their own axes 710 as well as the axis of the suture 712. One advantage of the planetary cutter system 700 is that it allows for the cutting of a helical array of barbs without twisting the suture 702 before cutting.

Opposing forces of cylindrical cutters 708 stabilize the suture 702 without the need for an additional vise apparatus. Three or more cylindrical cutters 708 may be used without departing from the scope of the present invention. In addition, opposing barb segments may be formed by engaging another planetary cutter 700 having appropriate cylindrical cutters 708 having spiral cutting edges 706 that rotate in an opposing direction to the original cylinders.

This method of barb formation allows access to the entire circumference of the suture. Breaks in spiral blade 706 prevent barbs from being shaved off the surface of the suture 702 after formation. Those skilled in the art will appreciate that the planetary cutter 700 may also comprise a ring gear (not shown) to apply rotational force to the cutters 708. Further, the ring gear may be driven in such a manner that the planetary cutter 700 traverses the longitudinal axis of the suture to form barbs of a desired length of suture without movement of the suture. Alternatively, the planetary cutter 700 may be stationary with the suture 702 being drawn through the rotating cutters 708. These and other variations of the planetary cutter 700 are considered within the scope of the invention.

While the invention has been described in connection with what is considered to be the most practical and preferred embodiment, it should be understood that this invention is not limited to the disclosed embodiments, but on the contrary, is intended to cover various modifications and equivalent arrangements included within the spirit and scope of the appended claims.

We claim:

1. A method of forming a barbed suture comprising the steps of:
   threading a filament from a filament supply through a filament tensioner and through a first and second collet; closing the first and second collets; cutting barbs in at least a first direction into the filament; rotating at least one of the collets in a first direction to twist the filament; opening the collets; advancing the filament using a filament grasping tool; closing the collets; and severing the filament having barbs cut in to form a suture.

2. The method of claim 1, further comprising a step of annealing the suture.

3. An apparatus for forming a barb on a suture comprising: at least one blade; a tensioning vise for supporting the suture; and a movable plate upon which the at least one blade and the tensioning vise are mounted, wherein the movable plate causes the vise to tension the suture, and develops a cutting motion for the at least one blade.

4. An apparatus for forming a barb on a suture comprising: at least one blade; a linkage system for causing the at least one blade to describe a substantially circular path during a cutting motion; and a drive gear system for imparting rotational force to the linkage system.

5. A barb cutting system comprising: a plurality of cylindrical cutters arranged in a planetary arrangement; and a plurality of cutting surfaces formed on the cylindrical cutters, wherein the cylindrical cutters rotate about their own axes while simultaneously rotating about an axis of a suture to form barbs thereon.

6. The barb cutting system of claim 5 wherein a plurality of cutting surfaces are spirally orientated about a cylindrical cutter.

7. The barb cutting system of claim 5 comprising breaks between adjacent segments of cutting surfaces.

8. The barb cutting system of claim 5 having two cylindrical cutters.

9. The barb cutting system of claim 5 comprising a first cylindrical cutter comprising cutting surfaces that route in a first direction, and a second cylindrical cutter comprising cutting surfaces that route in a second direction that opposes the first direction.

10. The barb cutting system of claim 9 wherein a cylindrical cutter comprises spiral cutting edges.

11. The barb cutting system of claim 5 further comprising a ring gear to apply rotational force to a cylindrical cutter.

12. The barb cutting system of claim 5 further comprising a ring gear to move a cylindrical cutter transversely to a longitudinal axis of the suture.

13. The barb cutting system of claim 5 comprising a stationary cylindrical cutter.

14. A method of forming barbs in a filament, comprising providing a filament, directing a fluid jet from a high pressure source toward the filament, and cutting barbs in the filament with the fluid jet.

15. The method of claim 14 wherein the fluid comprises water.

16. The method of claim 14 wherein the fluid does not comprise water.

* * * * *